US010358419B2

(12) United States Patent
Echegoyen et al.

(10) Patent No.: US 10,358,419 B2
(45) Date of Patent: Jul. 23, 2019

(54) 1,3-DIPOLAR [70]FULLEROPYRROLIDINIUM IODIDE DERIVATIVES

(71) Applicants: Luis A. Echegoyen, El Paso, TX (US); Manuel Llano, El Paso, TX (US); Edison A. Castro-Portillo, El Paso, TX (US); Zachary Martinez, El Paso, TX (US)

(72) Inventors: Luis A. Echegoyen, El Paso, TX (US); Manuel Llano, El Paso, TX (US); Edison A. Castro-Portillo, El Paso, TX (US); Zachary Martinez, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/555,842

(22) PCT Filed: Mar. 10, 2016

(86) PCT No.: PCT/US2016/021650
§ 371 (c)(1),
(2) Date: Sep. 5, 2017

(87) PCT Pub. No.: WO2016/145134
PCT Pub. Date: Sep. 15, 2016

(65) Prior Publication Data
US 2018/0037548 A1 Feb. 8, 2018

Related U.S. Application Data

(60) Provisional application No. 62/132,164, filed on Mar. 12, 2015.

(51) Int. Cl.
*C07D 209/94* (2006.01)
*A61K 31/403* (2006.01)

(52) U.S. Cl.
CPC .......... *C07D 209/94* (2013.01); *A61K 31/403* (2013.01)

(58) Field of Classification Search
CPC .................................................. C07D 209/94
USPC .......................................................... 546/2
See application file for complete search history.

(56) References Cited

U.S. PATENT DOCUMENTS

| 6,204,391 | B1 | 3/2001 | Friedman et al. ......... 548/338.1 |
| 2011/0059529 | A1 | 3/2011 | Wilson .......................... 435/421 |
| 2011/0071202 | A1* | 3/2011 | Mashino .............. A61K 31/194 514/393 |
| 2013/0160827 | A1 | 6/2013 | Jen et al. ....................... 136/252 |

OTHER PUBLICATIONS

Maroto, Angew. Chem. Intl. Edn. 2011, 50, 6060-6064.*
Barre-Sinossi et al., 1983, "Isolation of a T-lymphotropic retrovirus from a patient at risk for acquired immune deficiency syndrome (AIDS)." *Science* 220:868-870.
Blair et al. "New small-molecule inhibitor class targeting human immunodeficiency virus type 1 virion maturation." *Antimicrob. Agents. Chemother.* 2009, 53, 5080.
Clavel et al., 1986, "Isolation of a new human retrovirus from West African patients with AIDS." *Science* 223:343-346.
Dalgleish et al., 1984, "T-lymphocyte T4 molecule behaves as the receptor for human retrovirus LAV." *Nature* 312: 767-768.
Freed, "HIV-1 assembly, release and maturation." *Nat. Rev. Microbiol.* 2015, 13, 484.
Gallo et al., 1984, "Frequent detection and isolation of cytopathic retroviruses (HTLV-III) from patients with AIDS and at risk for AIDS." *Science* 224:500-503.
Garcia-Rivera et al. "Implication of serine residues 271, 273, and 275 in the human immunodeficiency virus type 1 cofactor activity of lens epithelium-derived growth factor/p75." *J. Virol.* 2010, 84, 740.
Guyader et al., 1987, "Genome organization and transactivation of the human immunodeficiency virus type 2." *Nature* 326:662-669.
Hammerwskjold and Rekosh, 1989, "The molecular biology of the human immunodeficiency virus." *Biochem. Biophys. Acta* 989:269-280.
International Preliminary Report on Patentability in International Application No. PCT/US2016/021650 dated Sep. 21, 2017.
International Search Report and Written Opinion in International Application No. PCT/US2016/021650 dated Jun. 2, 2016.
Li et al. "PA-457: a potent HIV inhibitor that disrupts core condensation by targeting a late step in Gag processing." *Proc. Natl. Acad. Sci. U.S.A.* 2003, 100, 13555.
Lukoyanova et al. "1H NMR spectroscopic studies of the conformational isomers of pyrrolidinofullerenes." *Chem. Eur. J.* 2007, 13, 8294.
Maddon et al., "The T4 gene encodes the AIDS virus receptor and is expressed in the immune system and the brain." 1986, *Cell* 47:333-348.
Marota, et al., "Hierarchical selectivity in fullerenes" *Angewandte Chemie International Edition.* 50:6060-4, 2011.
McDougal et al., 1986, "Binding of HTLV-III/LAV to T4+ T cells by a complex of the 110K viral protein and the T4 molecule." *Science* 231:382-385.
Nguyen et al. "The prototype HIV-1 maturation inhibitor, bevirimat, binds to the CA-SP1 cleavage site in immature Gag particles." *Retrovirology.* 2011, 8, 101.
Salzwedel et al. "Maturation inhibitors: a new therapeutic class targets the virus structure." *AIDS. Rev.* 2007, 9, 162.
Schimer et al. "Triggering HIV polyprotein processing by light using rapid photodegradation of a tight-binding protease inhibitor." *Nat. Commun.* 2015, 6, 6461.
Varmus 1988, "Retroviruses." *Science* 240:1427-1439.
Zhou et al. "Inhibition of HIV-1 maturation via drug association with the viral Gag protein in immature HIV-1 particles." *J. Biol. Chem.* 2005, 280, 42149.
Zhou et al. "Small-molecule inhibition of human immunodeficiency virus type 1 replication by specific targeting of the final step of virion maturation." *J. Virol.* 2004, 78, 922.

* cited by examiner

*Primary Examiner* — Nizal S Chandrakumar
(74) *Attorney, Agent, or Firm* — Norton Rose Fulbright US LLP

(57) ABSTRACT

Certain embodiments are directed to $C_{70}$ fullerene derivatives N—N-dimethyl [70]fulleropyrrolidinium iodide. Certain further embodiments are directed to α, β and γ isomer of N—N-dimethyl[70]fulleropyrrolidinium iodide.

13 Claims, 14 Drawing Sheets

α isomer
Formula I

β isomer
Formula II mixture of
N-N-dimethyl[70]fulleropyrrolidinium iodide
isomers
Formula IV α isomer    β isomer    γ isomer

1,3-DIPOLAR [70]FULLEROPYRROLIDINIUM IODIDE DERIVATIVES

This Application is a national phase application under 35 U.S.C. § 371 of International Application No. PCT/US2016/021650, filed Mar. 10, 2016, which claims priority to U.S. Provisional Patent Application 62/132,164 filed on Mar. 12, 2015. Both applications are hereby incorporated by reference in their entirety.

BACKGROUND

Human immunodeficiency virus (HIV) infects and destroys the immune system of human body. HIV infects CD4$^+$ T cells, the lymphocyte that activates our immune system against numerous infections. As the number of CD4$^+$ T cells in the body decrease, cell mediated immunity decreases and an HIV infected person develops acquired immunodeficiency syndrome (AIDS). An HIV infected person becomes more susceptible to infections and cancers, even to those infections and cancer that rarely occur to a healthy individual.

The number of HIV infected individuals is increasing continuously over the years on a global scale, but currently there is no cure or effective vaccine against HIV virus. Currently highly active anti-retroviral therapy (HAART) is often used to treat AIDS. HAART consists of a combination of antiretroviral agents. Although HAART slows progression of the disease and decreases risk of death, adverse effects are very common due to large dose and long term administration. Moreover, drug-resistant viruses and advanced genomic mutation in HIV makes the therapy less effective.

There remains a need for additional therapeutics for treating HIV infection.

SUMMARY

Certain embodiments are directed to C$_{70}$ fullerene derivatives N—N-dimethyl [70]fulleropyrrolidinium iodide. Certain aspects are directed to α, β, and γ isomer of N—N-dimethyl[70]fulleropyrrolidinium iodide. FIG. 13 depicts representative formulas provided as Formula I and Formula II.

FIG. 14 depicts other embodiments directed to a mixture of N—N-dimethyl[70]fulleropyrrolidinium iodide isomers prepared by one or more steps selected from (a) refluxing a mixture of fullerene, N-methylglycine, and paraformaldehyde in toluene, (b) evaporating the solvent, (c) purifying the product remaining after solvent evaporation to obtain a mixture comprising of α, β, and/or γ N-Methyl[70]fulleropyrrolidines, (d) dissolving the mixture comprising of α, β, and/or γ N-Methyl[70]fulleropyrrolidines in methyl iodide, (e) separating the precipitate formed from the reaction mixture, and (1) washing the precipitate with an organic solvent to obtain N—N-dimethyl[70]fulleropyrrolidinium iodide isomers.

FIG. 15 depicts certain embodiments directed to the fullerene derivatives of N-Methyl[70]fulleropyrrolidines. Certain aspects are directed to α, β, and/or γ isomer of N-Methyl[70]fulleropyrrolidines.

Certain embodiments are directed to administration of one or more N—N-dimethyl [70]fulleropyrrolidinium iodide isomers to a subject for treating and/or reducing HIV infection. The isomers can be administered alone or in combination with other anti-HIV therapies. In a further aspect an α isomer of N—N-dimethyl[70]fulleropyrrolidinium iodide compound is administered to treat and reduce HIV infection. The α isomer of N—N-dimethyl[70]fulleropyrrolidinium can be administered alone or in combination with one or more N—N-dimethyl [70]fulleropyrrolidinium iodide isomers and/or other anti-HIV therapies. In a further aspect the β isomer of N—N-dimethyl[70]fulleropyrrolidinium iodide is administered to treat and reduce HIV infection. The β isomer of N—N-dimethyl[70]fulleropyrrolidinium can be administered alone or in combination with one or more N—N-dimethyl [70]fulleropyrrolidinium iodide isomers and/or other anti-HIV therapies. In another aspect the γ isomer of N—N-dimethyl[70]fulleropyrrolidinium iodide is administered to treat and reduce HIV infection. The γ isomer of N—N-dimethyl[70]fulleropyrrolidinium can be administered alone or in combination with one or more N—N-dimethyl [70]fulleropyrrolidinium iodide isomers and/or other anti-HIV therapies. In another aspect a mixture of N—N-dimethyl[70]fulleropyrrolidinium iodide isomers is administered to treat and reduce HIV infection. The mixture of N—N-dimethyl[70]fulleropyrrolidinium iodide isomers can be administered alone or in combination with other anti-HIV therapies. In certain aspects the mixture can comprise 5, 10, 20, 30, 30, 40, 50, 60, 70, 80, or 90%, including all values and ranges there between, of an α isomer of N—N-dimethyl[70]fulleropyrrolidinium iodide with respect to the total amount of N—N-dimethyl[70]fulleropyrrolidinium iodide. In a further aspect the mixture can comprise 5, 10, 20, 30, 30, 40, 50, 60, 70, 80, or 90%, including all values and ranges there between, of a β isomer of N—N-dimethyl[70]fulleropyrrolidinium iodide with respect to the total amount of N—N-dimethyl [70]fulleropyrrolidinium iodide. In still a further aspect the mixture can comprise 5, 10, 20, 30, 30, 40, 50, 60, 70, 80, or 90%, including all values and ranges there between, of a γ isomer of N—N-dimethyl[70]fulleropyrrolidinium iodide with respect to the total amount of N—N-dimethyl[70]fulleropyrrolidinium iodide.

In certain aspects one or more N—N-dimethyl[70]fulleropyrrolidinium iodide isomers are administered to a subject in need of an anti-HIV treatment. In certain aspects the isomers are administered within 1, 5, 10, 20, 30, or 60 minutes or hours of each other. In a further aspect the isomers are administered concurrently. In a further aspects the isomers are in the same formulation or composition.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, etc.).

"Subject", "individual," "host" and "patient" are used interchangeably herein, to refer to any animal, e.g., mammal, human or non-human. Generally, the subject is a mammalian subject. Examples of such subjects includes, but is not limited to humans, non-human primates, mice, rats, cattle, sheep, goats, pigs, dogs, cats, birds, deer, elk, rabbit, reindeer, deer, and horses, with humans being of particular interest.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention.

Throughout this application, the term "about" is used to indicate that a value includes the inherent variation of error for the device, the method being employed to determine the value, or the variation that exists among the study subjects.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

As used herein, the term "$IC_{50}$" refers to an inhibitory dose that results in 50% of the maximum response obtained.

The term half maximal effective concentration ($EC_{50}$) refers to the concentration of a drug that presents a response halfway between the baseline and maximum after some specified exposure time.

The terms "inhibiting," "reducing," or "prevention," or any variation of these terms, when used in the claims and/or the specification includes any measurable decrease or complete inhibition to achieve a desired result.

The use of the term "or" in the claims is used to mean "and/or" unless explicitly indicated to refer to alternatives only or the alternatives are mutually exclusive, although the disclosure supports a definition that refers to only alternatives and "and/or."

The use of the word "a" or "an" when used in conjunction with the term "comprising" in the claims and/or the specification may mean "one," but it is also consistent with the meaning of "one or more," "at least one," and "one or more than one."

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
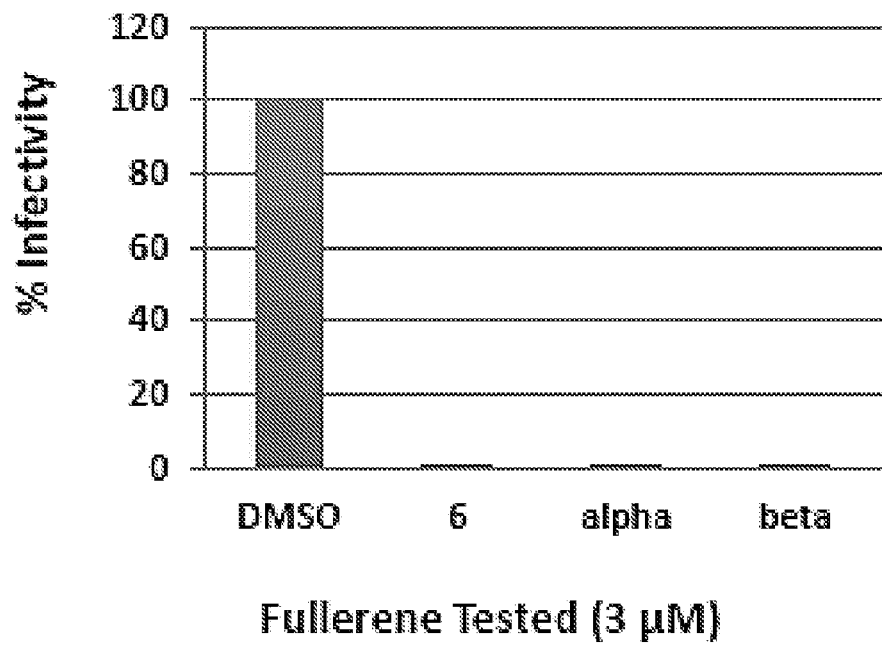
FIG. 1. Effect of fullerene derivatives on HIV-1 infectivity. HEK293T were co-transfected with plasmids expressing a replication defective HIV-1 virus that has the firefly luciferase cDNA replacing the nef gene and a deletion in the gene env, and the glycoprotein G of the Vesicular Stomatitis Virus (VSV-G). Transfected cells were washed 18 hrs later and cultured in the presence of DMSO, fullerene 6 (isomeric mixture, i.e., Formula IV), or either the alpha or the beta isomers of fullerene 6 (3 µM) for 36 hrs during HIV-1 production. Then, the single-round infection, VSV-G pseudotyped HIV-1 luciferase reporter virus present in the cell culture supernatant of these cells was concentrated through a 10% sucrose cushion by ultracentrifugation, and the amount of HIV-1 in the different viral samples was determined by quantifying HIV-1 p24 by ELISA. To determine the infectivity of the produced viruses, human CD4+ T cells (SupT1) were infected with equal amounts of viruses and four days later the levels of HIV-expressed luciferase activity were determined in the infected cells. Values detected in cells infected with the virus produced in the presence of DMSO were considered as 100%. Data indicate that fullerene 6 and the alpha and beta isomers potently blocked the infectivity of HIV-1.
Figure 2:
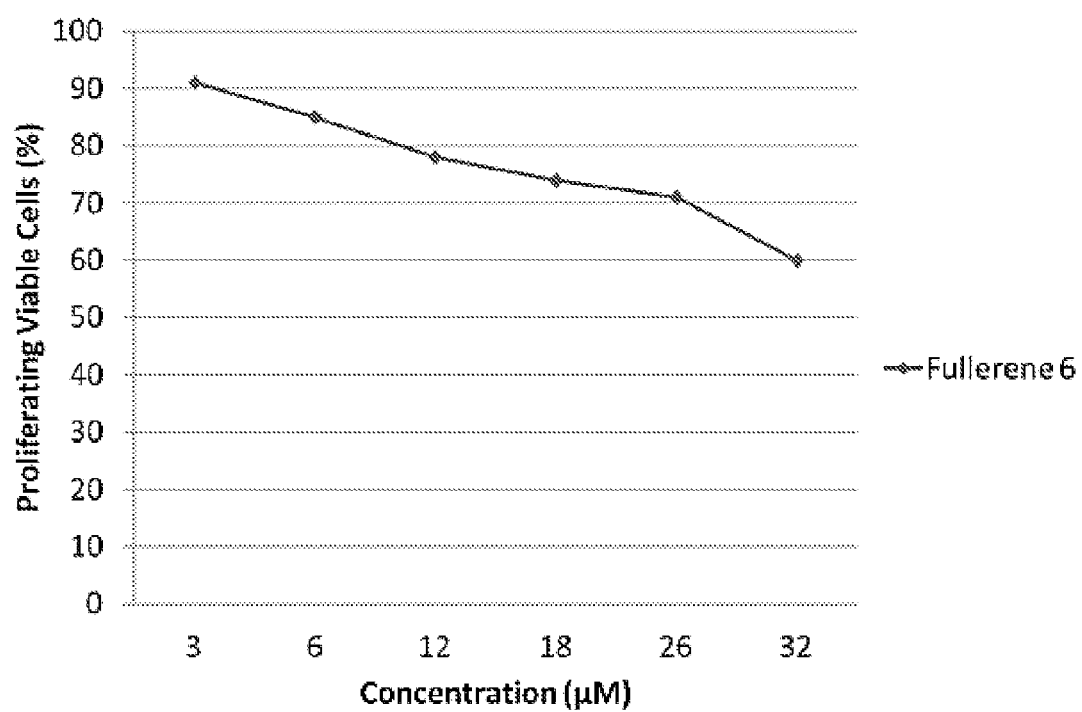
FIG. 2. Effect of fullerene 6 (isomeric mixture) on cell viability. Human CD4+ T cells (SupT1) were treated for 24 hrs with different doses of fullerene 6 or DMSO and then cellular viability was determined by the MTT assay that depends on the activity of cellular oxidoreductase enzymes. Activity in cells treated with DMSO was considered 100% activity. These results indicate that the lethal concentration 50 of fullerene 6 is over 32 µM.

Certain aspects described herein are directed to treatment for the human immunodeficiency virus (HIV) by administering $C_{70}$ fullerene derivatives. HIV is a pathogenic retrovirus and the causative agent of acquired immune deficiency syndrome (AIDS) and related disorders (Barre-Sinossi et al., 1983, *Science* 220:868-870; Gallo et al., 1984, *Science* 224:500-503). There are at least two distinct types of HIV: HIV-1 (Barre-Sinossi et al., 1983, *Science* 220:868-870; Gallo et al., 1984, *Science* 224:500-503) and HIV-2 (Clavel et al., 1986, *Science* 223:343-346; Guyader et al., 1987, *Nature* 326:662-669). Further, a large amount of genetic heterogeneity exists within populations of each of these types. Infection of human CD-4+ T-lymphocytes with an HIV virus leads to depletion of the cell type and eventually to opportunistic infections, neurological dysfunctions, neoplastic growth, and untimely death.

HIV is a member of the lentivirus family of retroviruses (Teich et al., 1984, *RNA Tumor Viruses*, Weiss et al., eds., CSH-press, pp. 949-956). Retroviruses are small enveloped viruses that contain a diploid, single-stranded RNA genome, and replicate via a DNA intermediate produced by a virally-encoded reverse transcriptase and RNA-dependent DNA polymerase (Varmus 1988, *Science* 240:1427-1439). The HIV viral particle consists of a viral core, made up of proteins designated p24 and p18. The viral core contains the viral RNA genome and those enzymes required for replicative events. Myristylated gag protein forms an outer viral shell around the viral core, which is, in turn, surrounded by a lipid membrane envelope derived from the infected cell membrane. The HIV envelope surface glycoproteins are synthesized as a single 160 kD precursor protein which is cleaved by a cellular protease during viral budding into two glycoproteins, gp41 and gp120. gp41 is a transmembrane protein and gp120 is an extracellular protein which remains noncovalently associated with gp41, possibly in a trimeric or multimeric form (Hammerwskjold and Rekosh, 1989, *Biochem. Biophys. Acta* 989:269-280).

HIV is targeted to CD-4+ T lymphocytes because the CD-4 surface protein acts as the cellular receptor for the HIV-1 virus (Dalgleish et al., 1984, *Nature* 312: 767-768, Maddon et al., 1986, *Cell* 47:333-348). Viral entry into cells is dependent upon gp120 binding the cellular CD-4+ receptor molecules, while gp41 anchors the envelope glycoprotein complex in the viral membrane (McDougal et al., 1986, *Science* 231:382-385; Maddon et al., 1986, *Cell* 47:333-348) and thus explains HIV's tropism for CD-4+ cells.

Fullerenes are carbon compounds composed entirely of carbon, in the form of a hollow sphere, ellipsoid, tube, or other shapes. Cylindrical fullerenes are called carbon nanotubes and spherical fullerenes are sometimes referred to as "buckyballs." $C_{70}$ fullerene or [70]fullerene is a cage like molecule composed of 70 carbon atoms joined together by single and double bonds to form a hollow sphere with 25 hexagonal and 12 pentagonal rings. The rings of the [70] fullerene can be chemically modified. In certain aspects [70]fullerenes can be modified with pyrrolidines.

N-Methyl[70]fulleropyrrolidines can be synthesized by refluxing a mixture of $C_{70}$ fullerene, N-methylglycine, and parafomaldehyde in toluene for a predefined period of time, e.g., 2 h or so. After refluxing the solution is evaporated under reduced pressure, and a crude product is purified by column chromatography on silica gel to afford the mixture of α, β, and γ N-Methyl [70]fulleropyrrolidines. α, β, and γ N-Methyl[70]fulleropyrrolidines can be separated using a Buckyprep column (10ID×250 mm, toluene, 2 mL/min).

N-Methyl[70]fulleropyrrolidines can be further modified to form N—N-dimethyl[70]fulleropyrrolidines. α-N—N-dimethyl[70]fulleropyrrolidinium iodide can be synthesized by dissolving α-N-Methyl[70]fulleropyrrolidine in methyl iodide with stirring at room temperature to give a black precipitate. The precipitate is collected by filtration, and then washed with $CS_2$, $CHCl_3$, toluene, MeOH, and acetone, in order, to isolate a black powder, α-N,N-dimethyl[70]fulleropyrrolidinium iodide.

β-N—N-dimethyl[70]fulleropyrrolidinium iodide can be synthesized by dissolving β-N-Methyl[70]fulleropyrrolidine in methyl iodide with stirring at room temperature to give a black precipitate. The precipitate is collected by filtration, and then washed, in order, with $CS_2$, $CHCl_3$, toluene, MeOH and acetone resulting in a black powder, β-N,N-dimethyl [70]fulleropyrrolidinium iodide.

γ-N—N-dimethyl[70]fulleropyrrolidinium iodide can be synthesized by dissolving γ-N-Methyl[70]fulleropyrrolidine in methyl iodide with stirring at room temperature to give a black precipitate. The precipitate is collected by filtration, and then washed, in order, with $CS_2$, $CHCl_3$, toluene, MeOH and acetone resulting in a black powder, γ-N,N-dimethyl[70]fulleropyrrolidinium iodide.

α, β, and γ-N—N-dimethyl[70]fulleropyrrolidinium iodide can be synthesized by dissolving a mixture of α, β and γ-N-Methyl[70]fulleropyrrolidine in methyl iodide with stirring at room temperature resulting in a black precipitate. The precipitate is collected by filtration, and then washed with $CS_2$, $CHCl_3$, toluene, MeOH and acetone in this order; resulting in a black powder, mixture of α, β, and γ-N—N-dimethyl[70]fulleropyrrolidinium iodide.

In certain embodiments described herein fullerenes and derivatives thereof can have antiviral activity and can be used for treatment of viral infections, such as HIV-infection. The infectivity of HIV was shown to be inhibited by N—N-dimethyl[70]fulleropyrrolidinium iodide, with a mixture resulting in 0.026%, α-N—N-dimethyl[70]fulleropyrrolidinium iodide resulting in 0.047%, and β-N—N-dimethyl[70]fulleropyrrolidinium iodide resulting in 0.003% infectivity as compared to control (100%) infectivity.

The inventors have found that viruses produced in the presence of low micromolar concentrations of the fullerene derivatives described herein exhibit a reduction in viral infectivity greater than 99%. However, in additional studies the compounds did not affect infectivity of mature virions, thus suggesting an effect on viral maturation. Analysis of Gag processing confirmed this mechanism of action, which is independent of the activity of protease as demonstrated by an in vitro enzymatic assay. As a result, $C_{70}$ fullerene derivatives potently impair viral infectivity of viruses harboring mutant proteases that developed resistance to multiple protease inhibitors in patients. Pull-down experiments using magnetic bead-immobilized compounds demonstrated that some $C_{70}$ fullerene derivatives strongly bind to the HIV capsid-spacer peptide 1 Gag proteolytic fragment, showing that this viral protein is the target. Comparison of the antiviral activity of $C_{70}$ fullerene derivatives to that of other small molecules and peptides that block maturation by binding to the HIV-1 capsid protein indicates that fullerene derivatives exhibit a new mechanism of action. In addition, some $C_{70}$ fullerene derivatives exhibited a 320-fold difference between their half maximum effective concentration and half lethal concentration, providing a broad potential pharmaceutical window. The $C_{70}$ cationic fullerene derivatives described herein are promising HIV-1 maturation inhibitor compounds.

Various chemical definitions related to such compounds are provided as follows.

As used herein, the term "halo" designates —F, —Cl, —Br or —I.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, —$CH_3$ (Me), —$CH_2CH_3$ (Et), —$CH_2CH_2CH_3$ (n-Pr), —$CH(CH_3)_2$ (iso-Pr), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), are all non-limiting examples of alkyl groups.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule. Pyrrolidine, also known as tetrahydropyrrole, is a saturated heterocycle with the molecular formula $(CH_2)_4NH$. It is a cyclic secondary amine.

The term "aryl" means a polyunsaturated, aromatic, hydrocarbon substituent. Aryl groups can be monocyclic or polycyclic (e.g., 2 to 3 rings that are fused together or linked covalently). One example of a polycyclic compound is the fullerenes. A fullerene is a molecule of carbon in the form of a hollow sphere, ellipsoid, tube, and many other shapes. Spherical fullerenes are also called buckyballs. Cylindrical fullerenes are called carbon nanotubes or buckytubes. Fullerenes are similar in structure to graphite, which is composed of stacked graphene sheets of linked hexagonal rings; but they may also contain pentagonal (or sometimes heptagonal) rings. The discovery of fullerenes greatly expanded the number of known carbon allotropes, which until recently were limited to graphite, diamond, and amorphous carbon such as soot and charcoal.

A particular fullerene is the $C_{70}$ fullerene. The $C_{70}$ fullerene consists of 70 carbon atoms. It is a cage-like fused-ring structure made of 25 hexagons and 12 pentagons, with a carbon atom at the vertices of each polygon and a bond along each polygon edge.

Various groups can be used as substituents to the pyrrolidines described herein. Substituents can be independently selected from: substituted or unsubstituted alkyl, or substituted or unsubstituted heteroalkyl. In certain aspects the pyrrolidines substituent is a methyl group.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

Pharmaceutical compositions of the invention are useful in the treatment or prevention of viral infections in humans and contain as an active agent one or more isoforms of N—N-dimethyl[70]fulleropyrrolidinium or N—N-dimethyl[70]fulleropyrrolidinium iodide. In certain aspects the pharmaceutical compositions can contain at least one other antiviral agent, such as reverse transcriptase inhibitors, protease inhibitor, inhibitors of mRNA processing, inhibitors of protein glycosylation, and inhibitors of viral fusion. Such agents include but are not limited to nucleoside analogs or chain terminators (e.g., dideoxynucleosides). Additional suitable therapeutic agents, or second HIV therapy, which may be used in combinational therapy include, but are not limited to 2-deoxy-D-glucose (2-dGlc), deoxynojirimycin, acycloguanosine, ribavirin (virazole), rifampicin (rifadin), adamantidine, rifabutine, ganciclover, (DHPG), fluoroiodoaracytosine, idoxurine, trifluorothymidine, adenine arabinoside (ara-A), ara-AMP, bromovinyldeoxyuridine, bromovinylarauracil (BV-araU by Bristol-Meyers Squibb (1-beta-D-arabinofuranoside-E-5-[2-bromovinyl]uracil)) rimantadine, arildone, diarylamidine, (S)-(p-nitrobenzyl-)6-thioinosine, and phosphonoformate.

The compounds and compositions described herein may be administered using techniques well known to those in the art. Preferably, agents are formulated and administered systemically. Techniques for formulation and administration may be found in "Remington's Pharmaceutical Sciences", 18th ed., 1990, Mack Publishing Co., Easton, Pa. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. In certain aspects administration is intravenous. For injection, the agents of the invention may be formulated in aqueous solutions, preferably in physiologically compatible buffers such as Hanks' solution, Ringer's solution, or physiological saline buffer.

A therapeutically effective dose refers to that amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population).

Pharmaceutical compositions containing the compounds described herein can be administered to a human patient, by itself, or in pharmaceutical compositions where it is mixed with suitable carriers or excipient(s) at doses to treat a viral infection, in particular HIV infection. Techniques for formulation and administration of the compounds of the instant application may be found in "Remington's Pharmaceutical Sciences," Mack Publishing Co., Easton, Pa., latest edition.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections; and transdermal, topical, vaginal and the like. Dosage forms include but are not limited to tablets, troches, dispersions, suspensions, suppositories, solutions, capsules, creams, patches, minipumps and the like.

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions, or emulsions in oily or aqueous vehicles, and may contain formulatory agents such as suspending, stabilizing, and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The antiviral activity exhibited by the compounds described herein may be measured, for example, by easily performed in vitro assays.

For the compounds of the present invention, alone or as part of a pharmaceutical composition, such doses are between about 0.001 mg/kg and 1 mg/kg body weight, preferably between about 1 and 100 μg/kg body weight, most preferably between 1 and 10 μg/kg body weight.

Therapeutically effective doses will be easily determined by one of skill in the art and will depend on the severity and course of the disease, the patient's health and response to treatment, the patient's age, weight, height, sex, previous medical history and the judgment of the treating physician.

In certain aspects a patient may have an HIV infection or be at risk of developing an HIV infection, or has been exposed to HIV. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

It is contemplated that any embodiment discussed in this specification can be implemented with respect to any method or composition of the invention, and vice versa. Furthermore, compositions of the invention can be used to achieve methods of the invention.

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of α, β and γ-N-Methyl[70]Fulleropyrrolidines

Figures 3A, 3B:
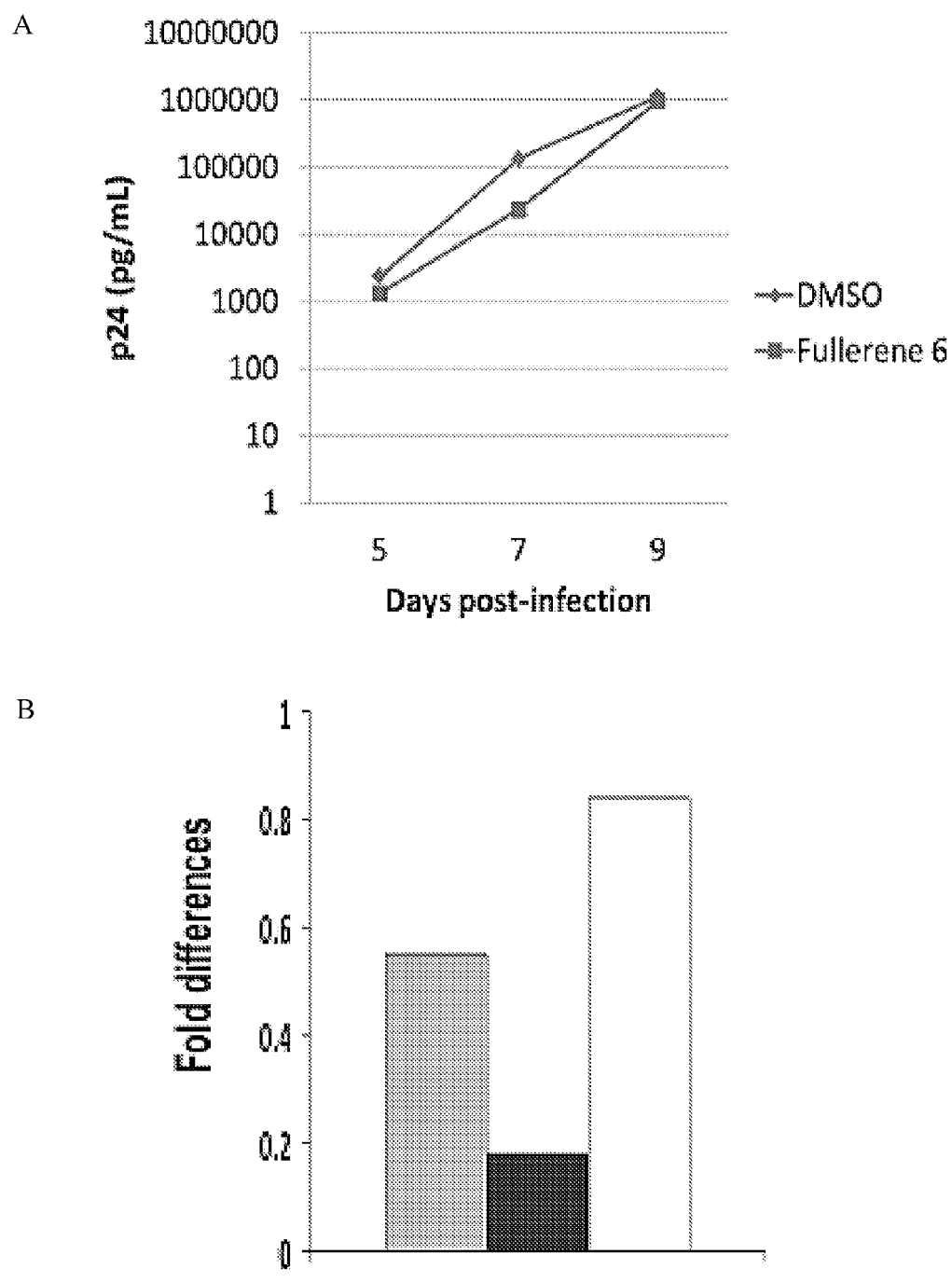
FIG. 3. Effect of fullerene 6 (isomeric mixture) on HIV-$1_{NL4-3}$ replication in human CD4+ T cells. SupT1 cells were infected with HIV-$1_{NL4-3}$ for 24 hours and extensively washed to remove the input virus. Then, the infected cells were exposed to fullerene 6 (6 µM) or DMSO (vehicle control) for 24 hrs, followed by a washing step to remove the treatments. Subsequently, the cells were grown for seven additional days and cell culture supernatant samples were taken periodically for quantification of HIV-1 p24 levels by ELISA. (a) Levels of HIV-1 p24 in the cell culture supernatant of infected cells treated with fullerene 6 or DMSO at different days post-infection. (b) Fold differences calculated using the data represented in FIG. 1. HIV-1 p24 levels measured in DMSO-treated cells were considered as 1. These findings indicate that a short treatment of HIV-1 infected cells with fullerene 6 was able to impair viral replication.
Figure 4:
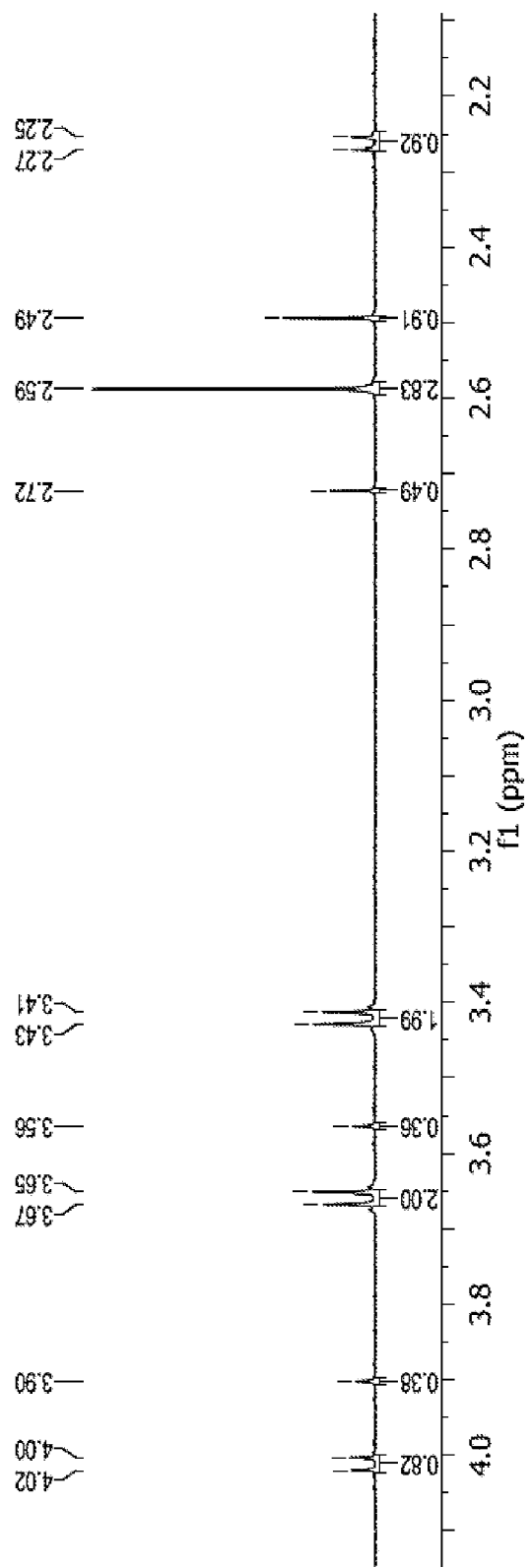
FIG. 4. $^1$H-NMR of the mixture of α, β, and γ-N-Methyl[70]fulleropyrrolidines.
Figure 5:
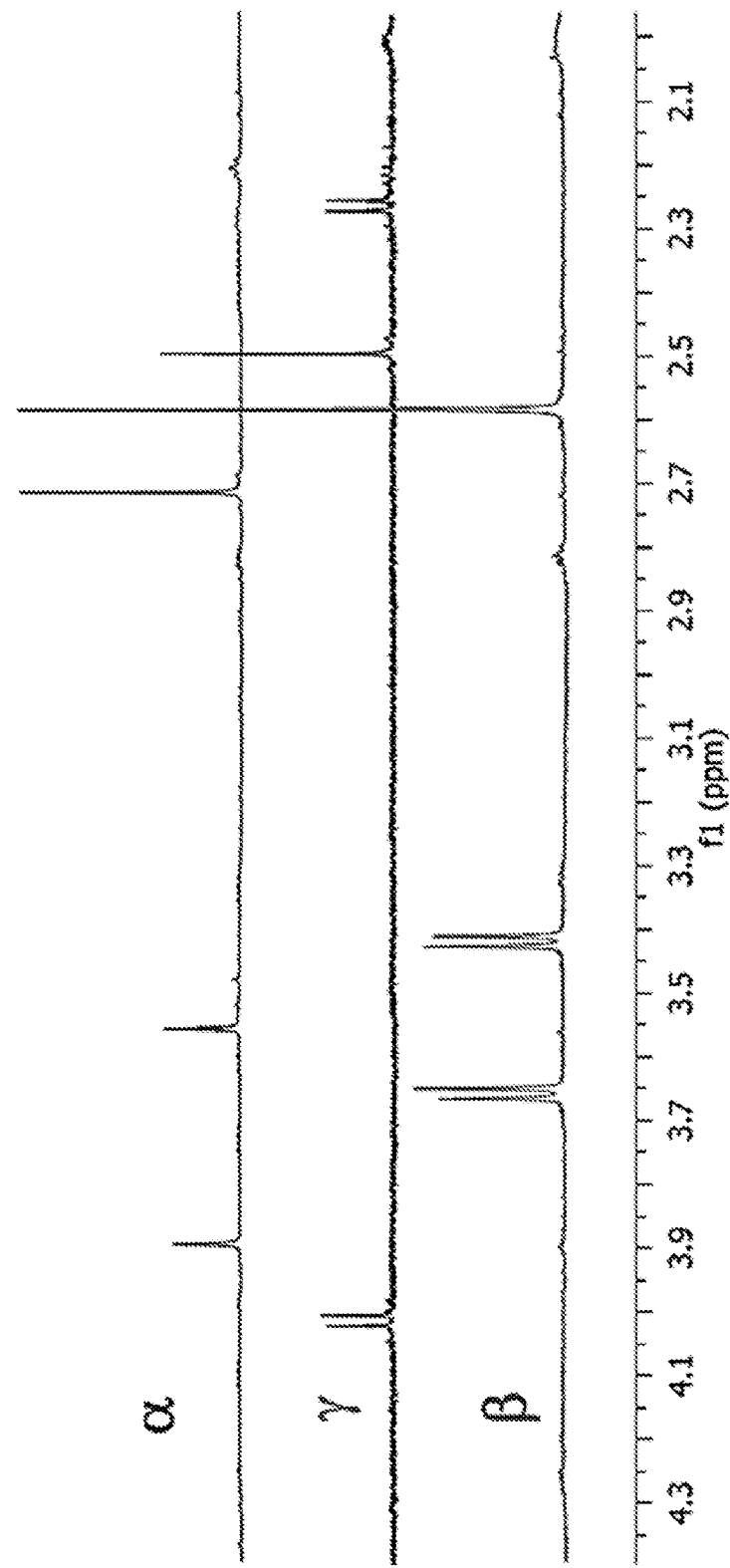
FIG. 5. $^1$H-NMR of α, β, and γ-N-Methyl[70]fulleropyrrolidines isomers after HPLC purification with Buckyprep column.
Figure 6:
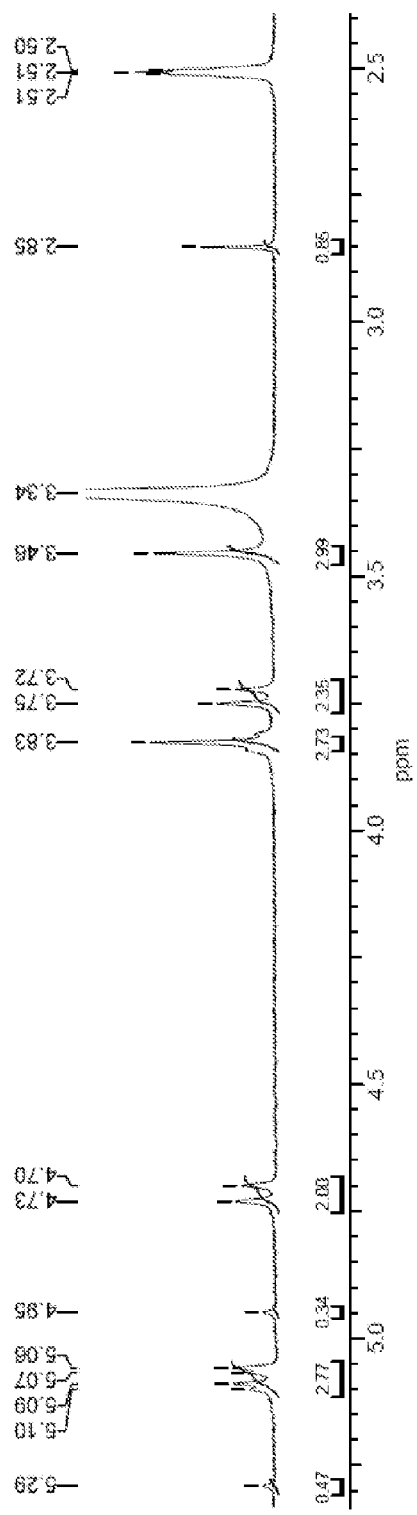
FIG. 6. $^1$H-NMR of the mixture of α, β, and γ-N—N-dimethyl[70]fulleropyrrolidium iodide.
Figure 7:
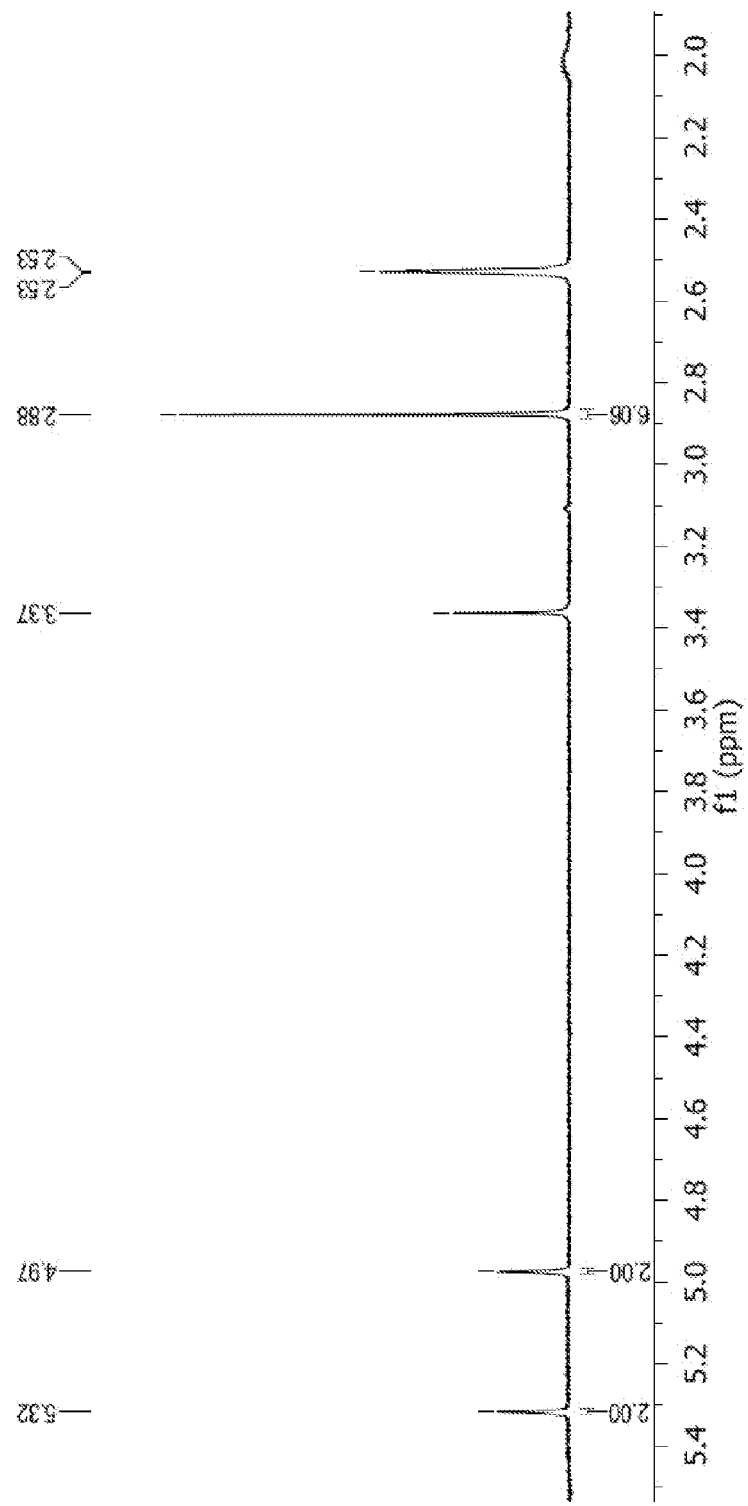
FIG. 7. $^1$H-NMR of α-N—N-dimethyl[70]fulleropyrrolidium iodide.
Figure 8:
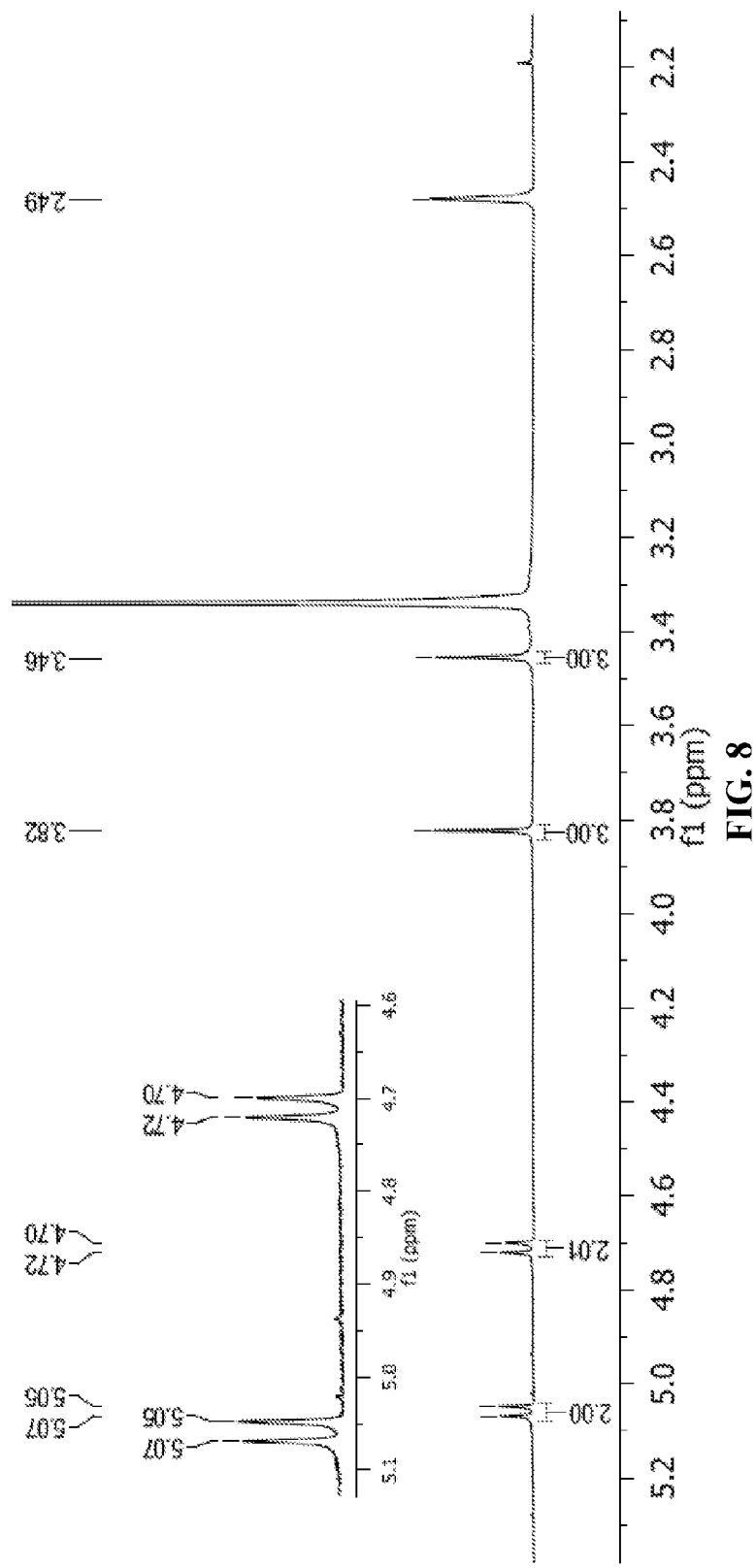
FIG. 8. $^1$H-NMR of β-N—N-dimethyl[70]fulleropyrrolidium iodides.

A mixture of $C_{70}$ fullerene (42 mg, 0.05 mmol), N-methylglycine (8.90 mg, 0.10 mmol), and parafomaldehyde (4.5 mg, 0.15 mmol) was refluxed in toluene (20 mL) for 2 h. The solution was evaporated under reduced pressure, and the crude product was purified by column chromatography on silica gel to afford the mixture of α, β, and γ N-Methyl [70]fulleropyrrolidines. α, β and γ N-Methyl[70]fulleropyrrolidines were separated using a Buckyprep column (10ID× 250 mm, toluene, 2 mL/min), which were obtained in a 35:53:12 ratio respectively. FIG. 3 and FIG. 4 shows the $^1$H-NMR spectra of the isomers before and after HPLC purification with Buckyprep column.

N-Methyl[70]fulleropyrrolidine (α-Isomer). $^1$H-NMR ($C_{52}$=CDCl$_3$, 600 MHz) δ: 3.90 (s, 2H), 3.56 (s, 2H), 2.72 (s, 3H) ppm; m/z: 898.025.

N-Methyl[70]fulleropyrrolidine (β-isomer). 1H-NMR (CS$_2$=CDCl$_3$, 600 MHz) δ: 3.66 (d, J=9.62 Hz, 2H), 3.42 (d, J=9.62 Hz, 2H), 2.59 (s, 3H) ppm; m/z: 898.110.

N-Methyl[70]fulleropyrrolidine (γ-isomer). $^1$H-NMR (CS$_2$=CDCl$_3$, 600 MHz) δ: 4.01 (d, J=9.62 Hz, 2H), 2.49 (s, 3H), 2.28 (d, J=9.62 Hz, 2H) ppm; m/z: 898.410.

Example 2

Synthesis of α-N—N-Dimethyl[70]Fulleropyrrolidinium Iodide

α-N-Methyl[70]fulleropyrrolidine (10 mg, 0.01 mmol) was dissolved in methyl iodide (10 mL) and stirred for 48 h at room temperature to give a black precipitate. The precipitate was collected by filtration, and then washed with CS$_2$, CHCl$_3$, toluene, MeOH and acetone in this order; to afford a black powder, α-N,N-dimethyl[70]fulleropyrrolidinium iodide.

α-N,N-dimethyl[70]fulleropyrrolidinium iodide. $^1$H-NMR (DMSO$_{d-6}$, 600 MHz) δ: 5.32 (s, 2H), 4.97 (s, 2H), 2.88 (s, 3H) ppm; m/z: 912.160.

Example 3

Synthesis of β-N—N-Dimethyl[70]Fulleropyrrolidinium Iodide

β-N-Methyl[70]fulleropyrrolidine (10 mg, 0.01 mmol) was dissolved in methyl iodide (10 mL) and stirred for 48 h at room temperature to give a black precipitate. The precipitate was collected by filtration, and then washed with CS$_2$, CHCl$_3$, toluene, MeOH and acetone in this order; to afford a black powder, β-N,N-dimethyl[70]fulleropyrrolidinium iodide.

β-N,N-dimethyl[70]fulleropyrrolidinium iodide. $^1$H-NMR (DMSO$_{d-6}$, 600 MHz) δ: 5.06 (d, J=12.04 Hz, 2H), 4.72 (d, J=12.04 Hz, 2H), 2.59 (s, 3H) ppm; m/z: 912.310.

Example 4

Synthesis of α, β and γ-N—N-Dimethyl[70]Fulleropyrrolidinium Iodide

Mixture of α, β and γ-N-Methyl[70]fulleropyrrolidine (10 mg, 0.01 mmol) were dissolved in methyl iodide (10 mL) and stirred for 48 h at room temperature to give a black precipitate. The precipitate was collected by filtration, and then washed with CS$_2$, CHCl$_3$, toluene, MeOH and acetone in this order; to afford a black powder, mixture of α, β and γ-N—N-dimethyl[70]fulleropyrrolidinium iodide.

Example 5

[70] Fullerene Derivatives Inhibit HIV-1 Maturation in a Protease-Independent Manner, and Specifically Interact with the HIV-1 Capsid Protein A. Materials and Methods Solvents and reagents were obtained from commercial sources (Rieke Metals Inc., Nano-C Inc., Sigma-Aldrich and Fisher Scientific) and were used as received.

Compound Analysis

The NMR spectra were recorded using a JEOL 600 MHz spectrometer. MALDI-TOF mass spectra were obtained on a Bruker Microflex LRF mass spectrometer. The UV-vis-NIR spectra were recorded using a Cary 5000 UV-vis-NIR spectrophotometer.

Synthesis of $C_{70}$ Fullerene Derivatives N—N-dimethyl [70]fulleropyrrolidinium Iodide Synthesis of $C_{70}$ fullerene derivatives N—N-dimethyl [70]fulleropyrrolidinium iodide are as provided above.

Syntheses of Compounds 3 and 4

Malonyl chloride II (300 mg, ~2.00 mmol) or dichloride III (140 mg, ~1.00 mmol) was added to a stirred solution of 5-hexyn-1-ol (200 mg, ~2.00 mmol) I and trimethylamine (TEA) (250 mg, ~2.50 mmol) in dry THF (15 mL) at room temperature, the reaction was stirred at this temperature overnight. The solution was evaporated under reduced pressure and the corresponding compounds 3 and 4 were purified using a column chromatography on silica gel and a hexane: ethyl acetate (5:1) mixture. KMnO$_4$ solution was used as the revelator for the TLC plates.

Scheme S1. Synthesis of compounds 3 and 4.

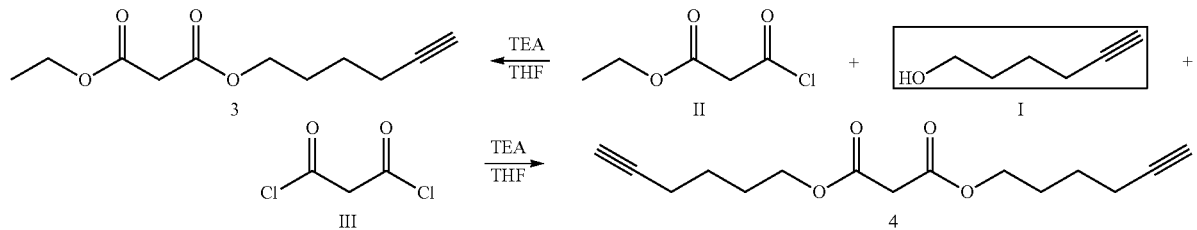

Figure 16:
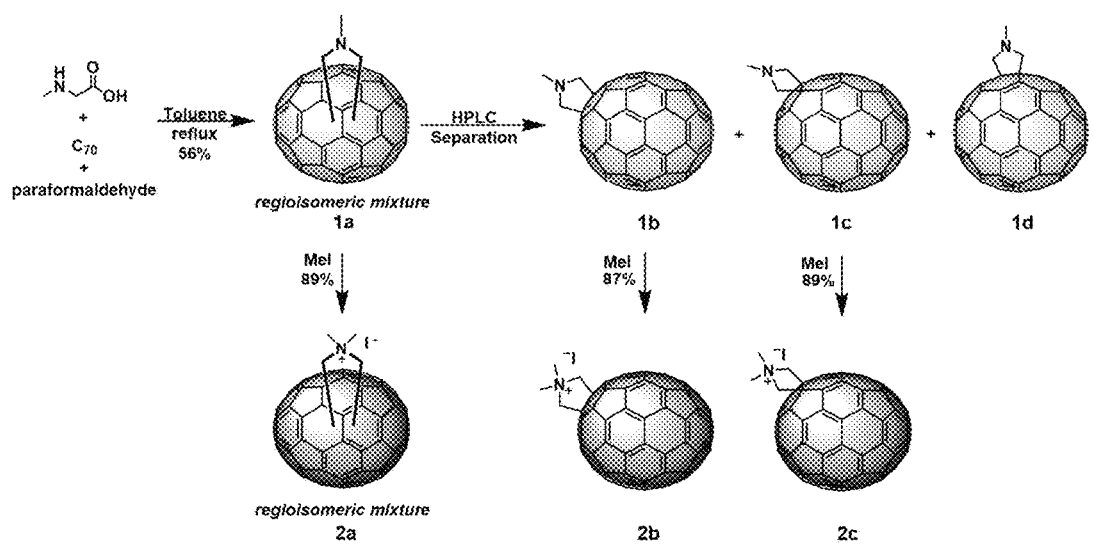
FIG. 16 depicts syntheses of $C_{70}$-(N,N-dimethylpyrrolidinium iodide) derivatives 2a-c. α isomers (1b and 2b), β isomers (1c and 2c) and 1d γ isomer.

FIG. 16 Depicts Syntheses of $C_{70}$—(N,N-dimethylpyrrolidinium Iodide) 2a-c The pure isomers 1b-d and the regioisomeric mixture 1a were each dissolved in methyl iodide (6 mL) and stirred for 48 h at room temperature to give a black precipitate. The precipitate was collected by filtration, and washed with $CS_2$, $CHCl_3$, toluene, MeOH and acetone, in this order, to give the corresponding $C_{70}$—(N,N-dimethylpyrrolidinium iodide) 2b,c and those of the regioisomeric mixture of 2a (Scheme 1). The ratio of the monoadducts in the mixture was 25:64:11 ($\gamma$:$\beta$:$\alpha$) as determined by $^1$H NMR, and their molecular masses were determined by matrix assisted laser desorption ionization-time of flight (MALDI-TOF).

Figure 17:
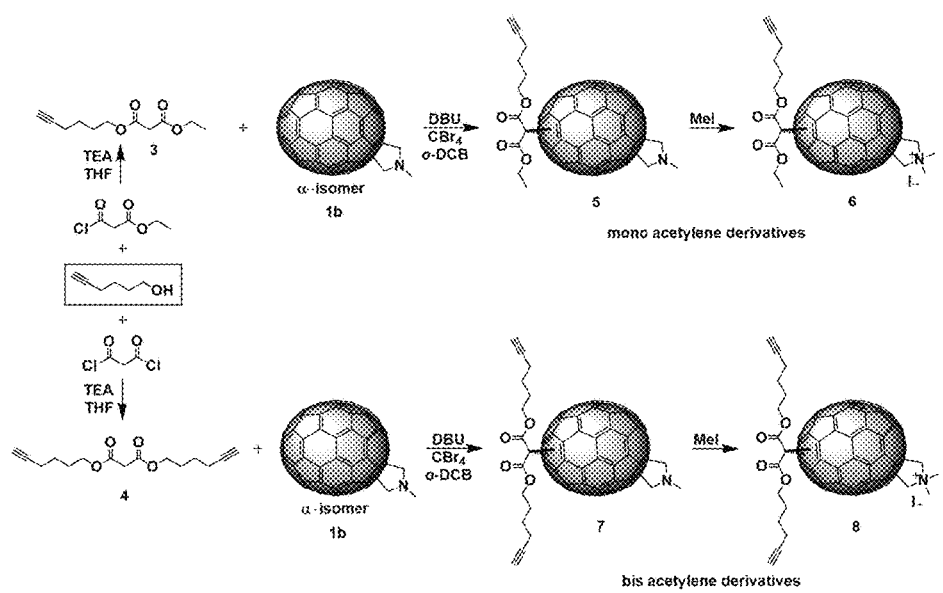
FIG. 17 depicts synthesis of $C_{70}$ mono and bis acetylene derivatives 5-8.

FIG. 17 Depicts Syntheses of $C_{70}$ Mono and Bis Acetylene Derivatives 5-8

Compounds 3 and 4 were synthesized according to procedures previously reported (Pereira de Freitas et al. *Tetrahedron.* 2008, 64, 11409). DBU (0.025 mL, 0.172 mmol) was added to a stirred solution of 1b (30 mg, 0.033 mmol), $CBr_4$ (0.331 mg, 0.100 mmol), and 3 or 4 (0.066 mmol) in toluene (20 mL) at room temperature. The solution was stirred overnight at this temperature, then it was evaporated under reduced pressure, and the mixture of bis-adducts was isolated by column chromatography on silica gel using toluene:ethyl acetate (10:1) as eluent. The first fraction after the starting material corresponded to the mixture of bis-adducts 5 or 7, respectively. Compounds 5 and 7 were separately dissolved in methyl iodide (6 mL) and stirred for 48 h at room temperature to give a brown precipitate. The precipitate was collected by filtration, and washed with $CS_2$, $CHCl_3$, toluene and acetone, in this order, to give the corresponding salts 6 and 8.

Magnetic Beads-Immobilized Fullerene (MBIF) Derivatives

Immobilized fullerene derivatives were prepared by click chemistry using a freshly prepared copper catalyst solution $CuSO_4$ (10 mmol/L) and ascorbic acid (20 mmol/L) in $H_2O$:THF (1:1) ratio. Then, one equivalent of azide with one equivalent of alkyne or half equivalent of bis alkyne were added and the resulting mixture was shaken for 6 h at room temperature. Finally, the immobilized fullerene derivatives were washed with water and stored in DMSO at 4° C. until used.

Pulldown Assay $3\times10^6$ HEK293T cells were plated in a T75 $cm^2$ tissue culture flask and transfected the next day with 20 μg of the Gag-Pol expression plasmid ΔR8.9 by the calcium-phosphate precipitation method. After 18 h, the transfection medium was replaced with fresh medium, and 24 h later the cells were washed in 1×PBS and lysed in 500 μL of 0.5% Triton in 1×PBS. The cell lysate was incubated on ice for 15 min, centrifuged at 22000 g for 10 min, and the supernatant was incubated with 50 μL of magnetic beads for 1 h at 4° C. to remove proteins binding non-specifically to the beads. 50 μL of the precleared lysate were saved as input sample, and 150 μL were mixed with 100 μL of non-functionalized magnetic beads or functionalized with fullerene derivatives 6 or fullerene derivatives 8. Beads and cell lysates were then rotated overnight at 4° C., followed by one 5 min wash using 0.5% Triton in 1×PBS. Washed beads were boiled 10 min at 100° C. in 50 μL of 2× Laemmli buffer, and the eluted proteins were analyzed by immunobloting with an anti HIV-1 p24 monoclonal antibody as described below.

Plasmids

The plasmids used to generate retroviral vectors were described previously (Llano et al. *Science.* 2006, 314, 461). HIV-1-derived vectors were produced using pHIV luc and pMD.G. pHIV Luc was derived from pNL4-3.Luc.R-E (He et al. *J. Virol.* 1995, 69, 6705) by introducing a deletion in the env open reading frame. pMD.G encodes the Vesicular Stomatitis Virus glycoprotein G (VSV-G).

Cell Lines

SupT1 and HEK293T cells were grown in RPMI 1640 and in DMEM, respectively. All culture media were supplemented with 10% of heat-inactivated fetal calf serum, 2 mM L-glutamine and 1% penicillin/streptomycin.

Generation of Retroviruses

Procedures previously described (Garcia-Rivera et al. *J. Virol.* 2010, 84, 740) were followed. Briefly, HEK293T cells were co-transfected with the corresponding plasmids by the calcium-phosphate precipitation method. After 18 h the transfection medium was replaced with fresh medium containing no drug, fullerene derivatives 2a-c, Indinavir, or DMSO (vehicle control). The cells were cultured for 48 h until the viral supernatant was harvested and filtered. Single-round infection viral vectors were further concentrated by ultracentrifugation.

VSV-G-pseudotyped HIV-derived reporter virus expressing firefly luciferase (HIVluc) was prepared by co-transfection of 15 μg of pHIV luc and 5 μg of pMD.G. HIV-1 wild type viruses were produced by transfection of 15 μg of the corresponding expression plasmids.

Single-Round Infectivity Assay

SupT1 cells were plated at 1×10$^5$ cells in 500 µL of RPMI 1640 culture medium in 24-well plates and infected with HIVluc. 4 days post-infection, cells were collected by centrifugation at 1000 g for 6 min and the pellet resuspended in 200 µL of phosphate-buffered saline (PBS). Half of the sample was mixed with 100 µL of luciferase substrate (Bright-Glow™ Luciferase Assay System, Promega) and the other half with 100 µL of cell viability substrate (CellTiter-Glo® Assay, Promega). Cell lysates were incubated for 10 min at room temperature in the dark and then luminescence was measured in triplicate in 50 µL-samples using a microplate luminometer reader (Thermo Scientific, Luminoskan Ascent).

HIV-1 Replication Assays

SupT1 cells were infected with HIV-1$_{NL4-3}$ (2.1 ng of HIV-1 p24) in the presence of the fullerene derivatives 2a-c or DMSO. 24 h after infection, the cells were extensively washed and viral replication was monitored by HIV-1 p24 quantification by ELISA.

Cellular Viability Assay

1×10$^4$ SupT1 cells were plated in a 96-well plate in 100 µL RMPI1640 culture media and left untreated or treated with fullerene derivatives 2a-c, DMSO (control), or 2 mM hydrogen peroxide (positive control). Fullerene derivatives 2a-c were evaluated at a concentration that ranged from 3 µM to 32 µM. The cells were cultured in the presence of the indicated compounds for 24 h and then 20 µL of the MTS were added to each well of cells. Incubation with the reagent for an additional 3 h was allowed. The colored formazan product was measured by absorbance at 490 nm with a reference wavelength of 650 nm using a microplate reader (SpectraMax 190, Molecular Devices). Control wells containing the same volumes of culture medium and MTS reagent were used to subtract background absorbance.

Immunoblotting

Proteins of HIV-1 p24-normalized amounts of virions (0.38 pig) were resolved by 13% SDS-PAGE and transferred overnight to PVDF membranes at 100 mAmp at 4° C. Membranes were blocked in TBS containing 10% milk for 1 h and then incubated in the corresponding primary antibody diluted in TBS-5% milk-0.05% Tween 20 (antibody dilution buffer) overnight at 4° C. HIV-1 p24 was detected with anti-p24 obtained from the NIH AIDS Reagent Program (Catalog #1513). HIV-1 integrase was detected with anti-integrase (Catalog # sc-69721, Santa Cruz Biotechnology). Primary antibody-bound membranes were washed in TBS-0.1% Tween 20 and all bound antibodies detected with goat anti-mouse IgG-HRP (1/2000, KPL, 074-1806) followed by chemo-luminescence detection.

HIV-1 Protease In Vitro Activity Assay

The ProAssay™ HIV-1 Protease Assay Kit was used as described in the supporting information. Briefly, HIV-1 protease and FRET peptide were treated or not with DMSO, fullerene derivatives 2a, b, and Indinavir. The reaction was measured by determining the Relative Fluorescing Intensity (RFI) with a fluorimeter using excitation/emission wavelengths of 490 nm/530 nm.

HIV-1 p24 ELISA

HIV-1 p24 levels were determined by a sandwich ELISA following manufacturer instructions. Briefly, 200 µL of the viral samples were diluted appropriately and incubated on the ELISA wells overnight at 37° C. Unbound proteins were removed by washing the wells 6 times with 200 µL of washing buffer, and bound HIV-1 p24 was detected by incubating each well with 100 µL of the anti-HIV-1 p24 secondary antibody for 1 h. Unbound antibodies were removed by washing and bound antibodies were detected by incubating each well with 100 µL of substrate buffer for 30 min at room temperature until the reaction was stopped by adding 100 µL of stop solution into each well. The absorbance of each well was determined at 450 nm using a microplate reader (Molecular Devices, Versa max microplate reader).

The effect of DMSO, compounds 2a, b (3 and 10 µM), and Indinavir (0.1 µM) on HIV-1 protease activity was measured using the ProAssay™ HIV-1 Protease Assay Kit. This assay uses purified recombinant HIV-1 protease and a fluorescence resonance energy transfer (FRET) peptide derived from the native p17/p24 cleavage site of HIV-1 protease on Gag. Briefly, HIV-1 protease (0.2 µL) and FRET peptide (final concentration 0.5 µM) were mixed in HIV-1 protease buffer supplemented with 1 mM DTT (final concentration) on ice and protected from light, and immediately transferred into a black 96-wells plate that contain the compounds being evaluated. The reaction was measured by determining the Relative Fluorescing Intensity (RFI) with a fluorimeter at excitation/emission wavelengths of 490 nm/530 nm every 5 min during 90 min.

B. Results

Synthesis of $C_{70}$ Pyrrolidinium Iodide Salts

The syntheses and purification of new water soluble $C_{70}$ pyrrolidinium iodide salts, derivatives 2b, c, was successfully accomplished, as well as of a regioisomeric mixture, 2a (Scheme 1). Due to the high polarity of compounds 2a-c, the best way to purify them was by high speed centrifugation (3000 rpm, 5 min) three times with every solvent ($CS_2$, $CHCl_3$, toluene, MeOH and acetone) in this specific order, to remove the unreacted starting materials. The yields obtained were in the range of 85-89%.

The purity of the α isomer 2b was confirmed by $^1$H NMR. Note that 2b is a mixture of diastereoisomers. Since methylation of the nitrogen atom makes it tetrahedral, the resulting mixture contains diastereoisomers (Lukoyanova et al. *Chem. Eur. J.* 2007, 13, 8294).

Two singlets at 4.97 and 5.32 ppm, each corresponding to two protons, are assigned to the methylene groups. One singlet at 2.88 ppm that corresponds to six protons was assigned to the two methyl groups. The β isomer 2c exhibits the same diastereomeric behavior as 2b. One AB quartet (ABq) at 4.89 ppm ($J_{AB}$=208.8, $\Delta\delta_{AB}$=12.7 Hz, 4H) was assigned to the methylene groups and the two singlets at 3.80 and 3.44 ppm, that correspond to three protons each, were assigned to the two methyl groups.

Compounds 1a-c were not soluble in polar solvents such as DMSO, DMF, THF, MeOH, acetone or water. However, their corresponding ammonium salts show high solubility in DMSO. The solubility of compounds 2a-c was determined by UV-vis spectroscopy in $H_2O$:DMSO (9:1). Linear calibration plots of absorbance vs concentration were obtained from known concentrations of compounds 2a-c in $H_2O$: DMSO. Dilution of saturated solutions of compounds 2a-c were used to determine the concentration by interpolation using the calibration curve. The solubility of compounds 2a-c in $H_2O$:DMSO (9:1) were 2.22, 1.92 and $2.52 \times 10^{-10}$ M, respectively.

Figures 9A, 9B, 9C:
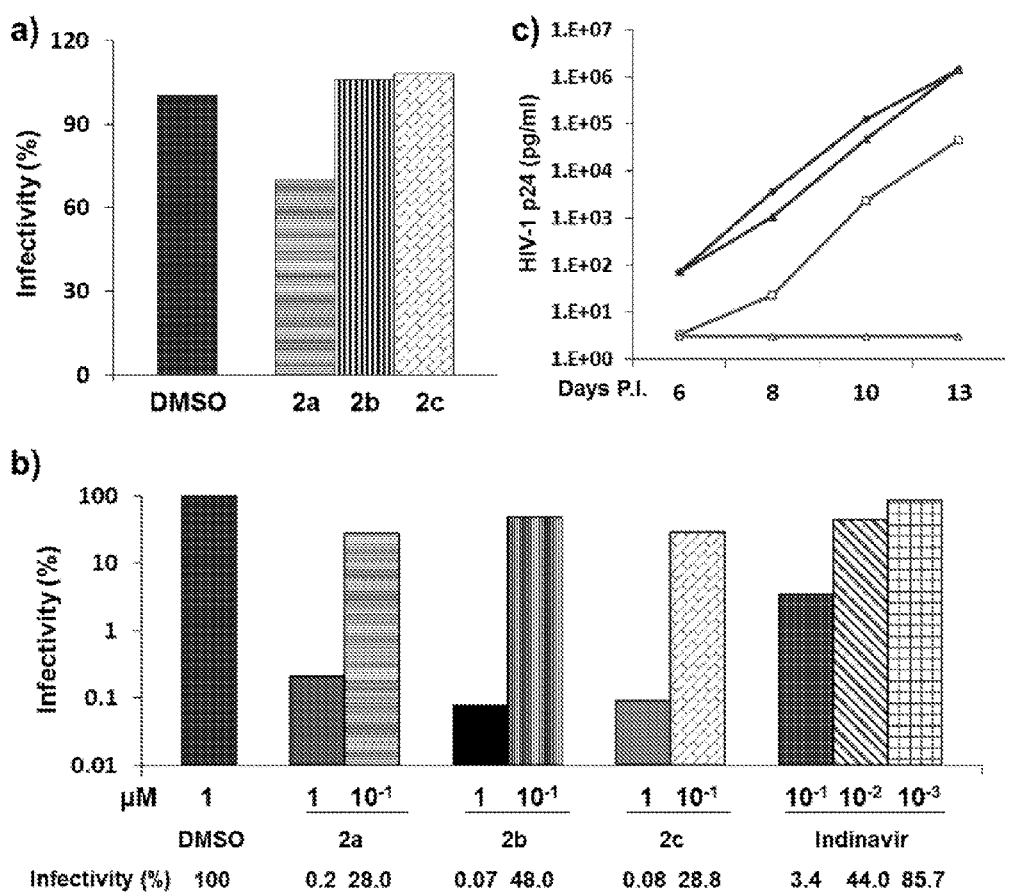
FIG. 9A-9C. Effect of fullerene derivatives 2a-c (also referred to as fullerene 6, which is an isomeric mixture of α, β, and γ N—N-dimethyl[70]fulleropyrrolidium iodides isomers) on HIV-1 infection and cell viability. (a) Effect on the early steps of the viral life cycle. (b) Effect on the late steps of the viral life cycle. Bars in (a) and (b) represent luciferase values normalized to ATP from one experiment. (c) Effect on HIV-1 replication. SupT1 cells were treated with DMSO (solid squares or triangles) or compound 2a (α-N—N-dimethyl[70]fulleropyrrolidium iodide) (3 µM) (open squares or triangles) at the time of infection with HIVNL4-3 2.1 ng, triangles, or 6.3 ng, squares, of p24.

Effect of Fullerene Derivatives 2a-c on the Early Stages of HIV-1 Life Cycle The inventors investigated the anti-HIV activities and the viral life cycle step affected by the cationic fullerene derivatives 2b, c and the regioisomeric mixture 2a. The effect of 2a-c on the infection of VSV-G pseudotyped HIV-1 single-round infection viruses expressing luciferase (HIVluc) was evaluated in the human CD4+ T cell line SupT1. The cells were exposed to fullerene derivatives 2a-c (10 μM) and infected with the reporter virus and 24 h later the compounds and the input virus were removed and three days later cellular luciferase and ATP levels were measured. Luciferase was normalized to ATP to adjust for cell viability and number. As expected, fullerene derivatives 2a-c did not affect the early stages of the viral life cycle (FIG. 9A).

Effect of Fullerene Derivatives 2a-c on the Late Stages of the HIV Life Cycle The effect of fullerene derivatives 2a-c on the late phase of the HIV-1 life cycle was further evaluated. HIVluc was produced in HEK293T cells in the presence of DMSO, fullerene derivatives 2a-c (0.1, and 1 μM), or Indinavir (0.1, 0.01, and 0.001 μM) and their infectivity was evaluated in single-round infection assays using SupT1 cells. Similar levels of HIV-1 p24 were found among these viruses indicating that fullerene derivatives did not affect LTR transcription, translation of viral proteins, immature particle assembly, viral budding, or cellular viability. The infectivity of viruses produced in the presence of $C_{70}$ fullerene derivatives 2a-c or Indinavir was dramatically reduced. Compounds 2a-c, caused more than 99% reduction of infectivity at 1 (FIG. 9B) and 3 μM (Data not shown), whereas it dropped to 72%, 52%, and 71% at 0.1 μM for fullerenes 2a-c, respectively. These data indicate that the drug concentration at which 50% of their maximum response was reached ($EC_{50}$) was approximately 0.1 μM. Comparison with Indinavir indicated that compounds 2a-c were between 6-10 fold less potent than this therapeutic drug that produced 96.6% and 56% inhibition at 0.1 μM and 0.01 μM, respectively. Indinavir only caused 14.3% inhibition at 0.001 μM (FIG. 9B).

The effect of $C_{70}$ fullerene derivatives on HIV-1 NL4-3 replication was also determined. SupT1 cells were infected with two amounts of virus (2.1 and 6.3 ng of HIV-1 p24) in the presence of the regioisomeric mixture 2a (3 μM) or DMSO. 24 h later the input virus and compounds were extensively washed and viral replication was followed by quantification of HIV-1 p24 in the cell culture supernatant by ELISA. Results in FIG. 9C show a potent inhibitory effect of the regioisomeric mixture 2a on HIV-1 replication. At the lowest multiplicity of infection (MOI), replication remains undetected for more than two weeks in cells infected in the presence of the regioisomeric mixture 2a. In contrast, the control infections produced ng of HIV-1 p24 one week after viral challenge. At the highest MOI, the regioisomeric mixture 2a reduced viral replication between 31 and 160-fold during the course of the experiment.

To confirm that fullerene derivatives 2a-c were non-toxic at the concentrations demonstrated to block HIV-1 infection, SupT1 cells were treated with different concentrations of fullerenes 2a-c and DMSO for 24 h and measured cell viability using the tetrazolium dye reduction assay (MTS assay). The drug concentration that kills approximately 50% of SupT1 cells ($LC_{50}$) was higher than 32 μM for each of these fullerene derivatives, indicating a 320-fold difference between their $LC_{50}$ and $EC_{50}$. These results also agree with findings indicating that fullerene derivatives 2a-c did not affect cell viability, as measured by ATP levels (data not shown), when SupT1 cells were treated with 10 μM of these compounds for 24 h during infection with HIV-1 luc (FIG. 9A).

Effect of Fullerene Derivatives 2a-c on HIV-1 Gag Processing

Figures 10A, 10B, 10C:
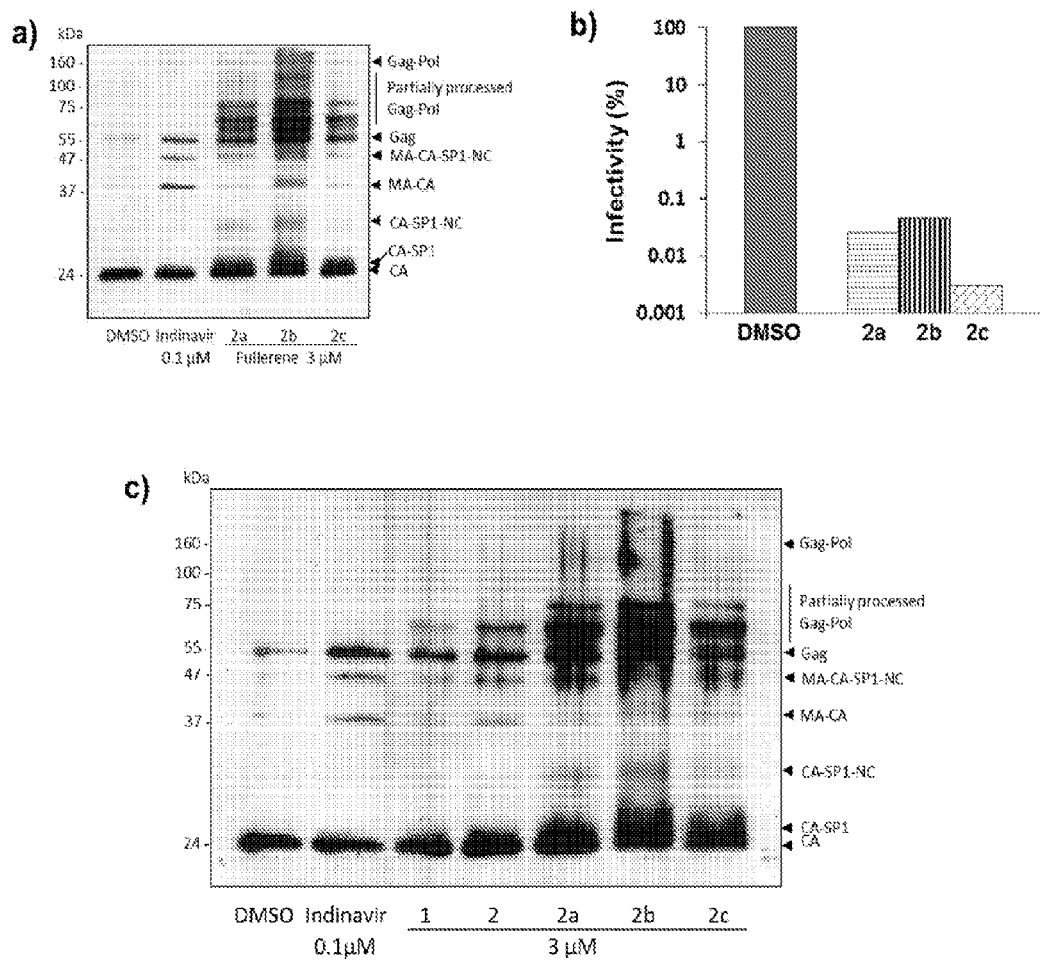
FIG. 10A-10C. Effects of $C_{70}$ fullerene derivatives 2a-c on HIV-1 Gag and Gag-Pol processing. (a) Immunoblot analysis of Gag and Gag-pol processing in virions. (b) Infectivity of virions evaluated in panel (a). SupT1 cells were infected with the viruses analyzed in (a) as described in FIG. 3b. Data in panels (a) and (b) are representative of two independent experiments. (c) Relative effect of $C_{70}$ (compounds 2a (α-N—N-dimethyl[70]fulleropyrrolidium iodide), 2b (β-N—N-dimethyl[70]fulleropyrrolidium iodide), and 2c (γ-N—N-dimethyl[70]fulleropyrrolidium iodide)) on Gag and Gag-Pol processing. Results are representative of two independent experiments. The identity of the Gag proteolytic fragments has been previously described (Sundquist and Krausslich, *Cold. Spring. Harb. Perspect. Med.* 2012, 2, a006924; Schimer et al. *Nat. Commun.* 2015, 6, 6461).

Data in FIG. 9 suggest that fullerenes 2a-c, block HIV-1 maturation. In order to define whether $C_{70}$ derivatives inhibit HIV-1 infection by similar mechanisms, the efficiency of Gag and Gag-Pol processing in virions produced in the presence of DMSO, fullerenes 2a-c (3 μM), and Indinavir (0.1 μM) was determined by immunoblot analysis with an anti-capsid (CA, p24) monoclonal antibody. Capsid is a domain in Gag, therefore, non- or partially processed Gag and Gag-Pol proteins containing CA are detected in this assay. Data in FIG. 10 indicate a pronounced decrease in Gag and Gag-Pol processing in the virions produced in the presence of $C_{70}$ fullerene derivatives that correlated with the decrease in infectivity observed in these same viruses (FIG. 10B).

$C_{70}$ fullerenes impair Gag and Gag-Pol processing at a higher magnitude than Indinavir. As well, fullerene-treated virions contain a larger proportion of Gag processing intermediates in contrast with virions produced in the presence of Indinavir. HIV-1 proteins in Gag are ordered from N- to the C-terminus as matrix (p17, MA, 17 kDa), capsid (p24, CA, 24 kDa), spacer peptide 1 (SP1, 2 kDa), nucleocapsid (NC, 7 kDa), spacer peptide 2 (SP2, 1 kDa), and late domain-containing protein P6 (P6, 6 kDa) (Sundquist and Krausslich, *Cold. Spring. Harb. Perspect. Med.* 2012, 2, a006924; Pettit et al. *J. Virol.* 1994, 68, 8017). Protease-mediated Gag processing occurs in a fixed order, resulting in several processing intermediates, some of which are indicated in FIG. 10A. Several CA-containing Gag fragments, presumably identified as CA-SP1-NC (~33 kDa) and CA-SP1 (~25 kDa)(Sundquist and Krausslich, *Cold. Spring. Harb. Perspect. Med.* 2012, 2, a006924), were enriched in the fullerene- but not in the Indinavir-treated virions. Therefore, these data suggest that $C_{70}$ fullerene derivatives 2a-c and Indinavir affect Gag and Gag-Pol processing by different mechanisms.

Relative Inhibitory Potency of $C_{70}$ Fullerene Derivatives 2a-c on HIV-1 Gag Processing $C_{70}$ fullerene derivatives have been reported to have anti-HIV-1 activity (Kornev et al. *Chem. Commun.* 2011, 47, 8298), but their relative potency was not evaluated in regards to the effect on Gag processing. Therefore, following the procedure described in FIG. 10A, the effect of $C_{70}$ derivatives on Gag processing were studied at a dose that potently inhibits HIV-1 infection (3 μM). Data in FIG. 10C show that the $C_{70}$ derivatives potently affected Gag and Gag-Pol processing.

Figures 11A, 11B, 11C, 11D:
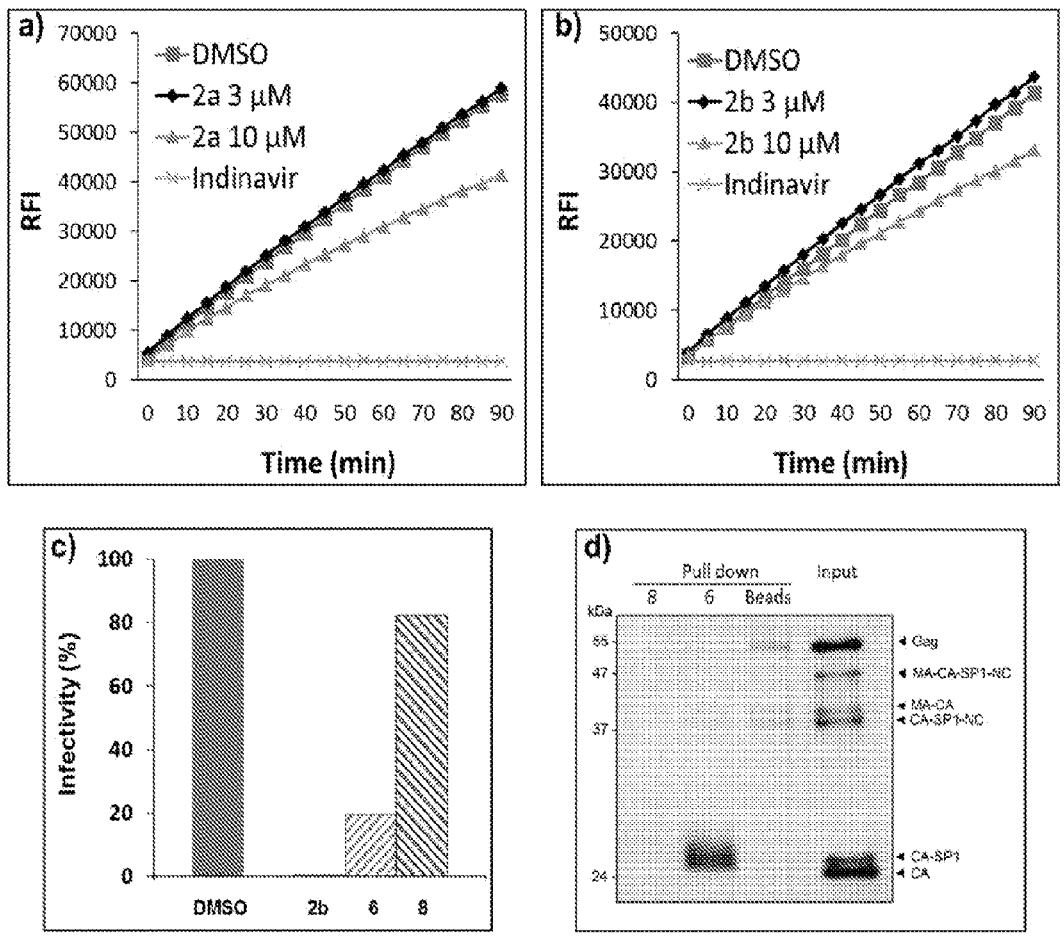
FIG. 11A-11D. Analysis of the mechanism of action of $C_{70}$ fullerene derivatives 2a,b. (a) Effect of compounds 2a and 2b in the in vitro activity of HIV-1 protease. The cleavage of an HIV-derived FRET peptide by recombinant HIV-1 protease in the presence of compounds 2a (a) and 2b (b) at 3 µM and 10 µM was determined by fluorescence measurements. (c) Effect on HIV-1 infection of fullerene 2b, and compounds 6 and 8 that were coupled to the beads used in (d). (d) Analysis of the interaction of HIV-1 Gag with beads coated with active or inactive fullerene derivatives 6 and 8, respectively.

Analysis of the Mechanism of Action of $C_{70}$ Fullerene Derivatives 2a-c in HIV-1 Maturation Gag processing can be affected by protease inhibition or by altering the conformation of the protease substrate (Freed, *Nat. Rev. Microbiol.* 2015, 13, 484; Sundquist and Krausslich, *Cold. Spring. Harb. Perspect. Med.* 2012, 2, a006924). Therefore, the effect of the $C_{70}$ fullerene derivatives 2a-c on the ability of recombinant HIV-1 protease to cleave a peptide derived from the native p17/p24 (MA-CA) cleavage site of protease on Gag were determined. $C_{70}$ derivatives 2a and 2b did not significantly affect HIV-1 protease activity at doses that strongly block HIV-1 infection (3 and 10 μM, FIG. 11A). Even at 40 a concentration that exceeds the $LD_{50}$, fullerene 2b only inhibited 24% of protease activity and reached 65% inhibition at 80 μM. Therefore, these results indicate that $C_{70}$ fullerene derivatives 2a, b are not protease but HIV-1 maturation inhibitors.

The fact that fullerene derivatives 2a-c generated more CA-containing Gag processing intermediates than Indinavir suggests that compounds 2a-c could bind to CA. Similarly, Bevirimat and related compounds that bind to the region flanking the CA-SP1 junction selectively produce the accumulation of this processing intermediate in the virion (Blair et al. *Antimicrob. Agents. Chemother.* 2009, 53, 5080.; Zhou et al. *J. Biol. Chem.* 2005, 280, 42149; Li et al. *Proc. Natl. Acad. Sci. USA.* 2003, 100, 13555; Nguyen et al. *Retrovirology.* 2011, 8, 101; Salzwedel et al. *AIDS. Rev.* 2007, 9, 162; Zhou et al. *J. Virol.* 2004, 78, 922). Therefore, the inventors explored the interaction of 2a-c with HIV-1 CA in the context of Gag and Gag-Pol polyproteins using a pull-down assay with $C_{70}$ fullerene derivative 2b as bait, followed by anti-CA immunoblot analysis. $C_{70}$ fullerene derivative 2b was functionalized with one or two acetylene groups, compounds 6 and 8 respectively, and then coupled to the azide magnetic beads via click chemistry. Infrared (IR) analysis showed that the $C_{70}$ derivatives were successfully coupled covalently to the beads. The IR spectrum of the magnetic beads coupled to fullerene 6 does not exhibit the azide or the acetylene stretching vibration band around 2100 $cm^{-1}$. However, new bands were observed between 900 to 1500 $cm^{-1}$, indicating the presence of the fullerene derivative moiety and as expected the intensity of the carbonyl (C=O) stretching band was increased. Additionally, the IR spectrum of this compound shows the characteristic —$CH_2$ and —$CH_3$ stretching bands between 2900 and 3000. Magnetic beads coupled to fullerene 8 showed similar IR characteristics.

To evaluate if the functionalization of 2b with malonates 3 and 4 disrupted its anti-HIV-1 activity, HIVluc was produced by transfection in HEK 293T in the presence of fullerene derivatives 2b, 6, 8 or DMSO. The infectivity of the produced viruses was evaluated in single-round infection assays in SupT1 cells. Data in FIG. 11C indicate that functionalization of fullerene 2b using a symmetric dihexynyl malonate 4 resulted in the total loss of its anti-HIV-1 activity. Fortunately, the inhibition activity was preserved for compounds 6, with only one acetylene group.

Lysates from HEK 293T cells transiently expressing HIV-1 Gag and Gag-Pol polyproteins were incubated overnight with magnetic beads with no fullerenes attached or beads containing active or inactive fullerene derivatives 6 and 8, respectively. Then, beads were washed and the bound proteins analyzed by immunoblot with an anti-p24 (HIV-1 CA) monoclonal antibody. Data in FIG. 11D demonstrate that a CA-containing Gag product of ~25 kDa, suggesting the CA-SP 1 fragment, strongly binds to beads containing active fullerene derivatives 6, but not to those with the inactive derivative 8 or no fullerene attached. Therefore, these results demonstrated the specific interaction of active fullerene derivative 6 with HIV-1 CA-SP1 protein. No other CA products were pulled-down suggesting that stable binding of fullerene derivatives 6 to CA-SP1 requires Gag processing.

Anti-Viral Activity of $C_{70}$ Fullerene Derivatives 2a on HIV-1 Molecular Clones Harboring Mutant Proteases Resistant to Protease Inhibitors Typically, HIV-1 maturation inhibitors block infection by HIV-1 strains resistant to protease inhibitors, indicating that this type of drugs would be excellent additions to current anti-HIV-1 therapy (Freed *Nat. Rev. Microbiol.* 2015, 13, 484; Sundquist and Krausslich, *Cold. Spring. Harb. Perspect. Med.* 2012, 2, a006924). In order to evaluate the effect of $C_{70}$ fullerene derivatives 2a on the infectivity of HIV-1 strains resistant to multiple protease inhibitors, HIVluc-derived viruses harboring a panel of protease inhibitor-resistant mutant proteases were produced by plasmid transfection in HEK 293T cells in the presence of DMSO, Indinavir (0.1 μM), or fullerene derivatives 2a (3 μM). The mutant viruses analyzed included 11803, 11806, 11807, 11808, and 11809 that are resistant to nelfinavir, Fosamprenavir, Saquinavir, Indinavir, Atazanavir, Lopinavir, Tipranavir, and Darunavir; and 11805 that is also resistant to these drugs except for Tipranavir and Darunavir. The protease (99 amino acids) in these viruses contains between 10 and 24 point mutations (Garcia-Rivera et al. *J. Virol.* 2010, 84, 740).

Figure 12:
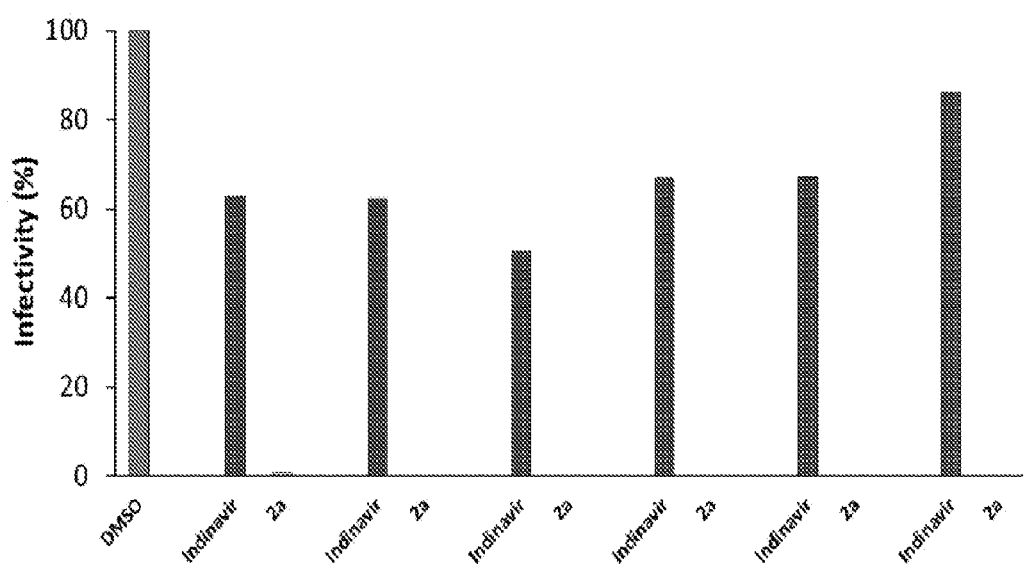
FIG. 12. Effect of the regioisomeric mixture 2a and Indinavir on the infectivity of HIVluc-derived viruses carrying protease mutants resistant to multiple clinically approved protease inhibitors.
Figure 13:
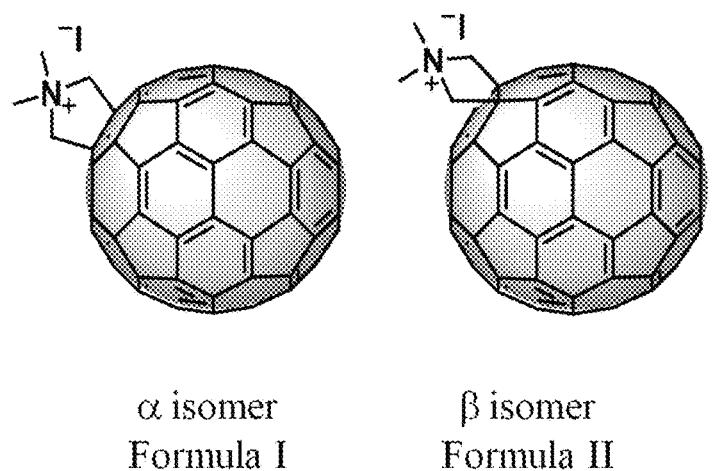
FIG. 13 depicts certain embodiments directed to $C_{70}$ fullerene derivatives N—N-dimethyl [70]fulleropyrrolidinium iodide. Representative formulas are provided as Formula I and Formula II.
Figure 14:
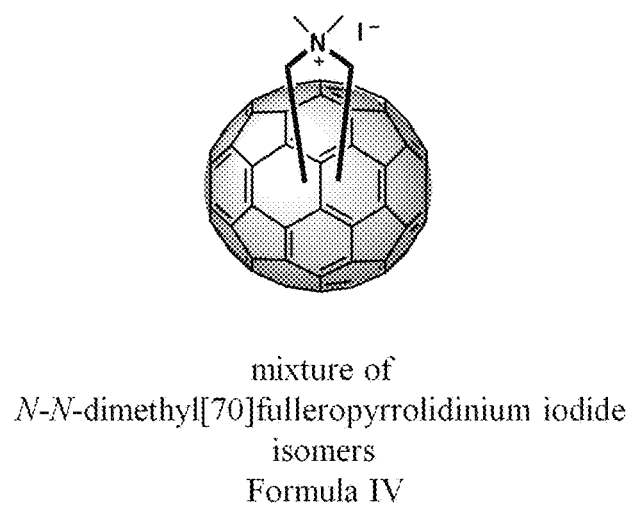
FIG. 14 depicts other embodiments directed to a mixture of N—N-dimethyl[70]fulleropyrrolidinium iodide isomers.
Figure 15:
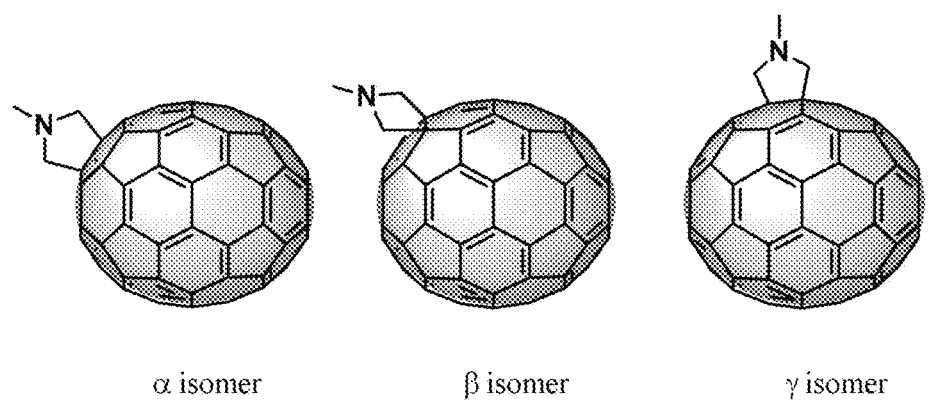
FIG. 15 depicts certain embodiments directed to the fullerene derivatives of N-Methyl[70]fulleropyrrolidines.

Produced viruses were normalized for p24 and used to infect SupT1 cells. Four days after infection, cellular ATP and luciferase levels were measured and luciferase normalized to ATP. Using this procedure, it was found that the regioisomeric mixture 2a potently inhibits all the multi protease inhibitor resistant viruses (FIG. 12) to a similar extent as reporter viruses harboring wild type protease.

As expected, Indinavir failed to significantly affect the infection of these viruses. These findings highlight the therapeutic potential of fullerene derivatives further supporting their protease-independent mechanism of action.

The invention claimed is:

1. A composition comprising at least one isomer of an α-N—N-dimethyl[70]fulleropyrrolidinium iodide, β-N—N-dimethyl[70]fulleropyrrolidinium iodide, or γ-N—N-dimethyl[70]fulleropyrrolidinium iodide.

2. The composition of claim 1, wherein the α-N—N-dimethyl[70]fulleropyrrolidinium iodide comprises 10 to 90% of the N—N-dimethyl[70]fulleropyrrolidinium iodide in the composition.

3. The composition of claim 1, wherein the β-N—N-dimethyl[70]fulleropyrrolidinium iodide comprises 10 to 90% of the N—N-dimethyl[70]fulleropyrrolidinium iodide in the composition.

4. The composition of claim 1, wherein the γ-N—N-dimethyl[70]fulleropyrrolidinium iodide comprises 10 to 90% of the N—N-dimethyl[70]fulleropyrrolidinium iodide in the composition.

5. The composition of claim 1, wherein the isomer is α-N—N-dimethyl[70]fulleropyrrolidinium iodide.

6. The composition of claim 1, wherein the isomer is β-N—N-dimethyl [70]fulleropyrrolidinium iodide.

7. The composition of claim 1, wherein the isomer is γ-N—N-dimethyl[70]fulleropyrrolidinium iodide.

8. The composition of claim 1, wherein the isomer is an α-N—N-dimethyl[70]fulleropyrrolidinium iodide and β-N—N-dimethyl[70]fulleropyrrolidinium iodide.

9. The composition of claim 8, where in the ratio of α-N—N-dimethyl[70]fulleropyrrolidinium iodide to β-N—N-dimethyl[70]fulleropyrrolidinium iodide is 0.1 to 10.

10. The composition of claim 1, wherein the isomer is an α-N—N-dimethyl[70]fulleropyrrolidinium iodide, β-N—N-dimethyl[70]fulleropyrrolidinium iodide, and γ-N—N-dimethyl[70]fulleropyrrolidinium iodide.

11. The composition of claim 1, wherein the isomer is an α-N—N-dimethyl[70]fulleropyrrolidinium iodide and γ-N—N-dimethyl[70]fulleropyrrolidinium iodide.

12. The composition of claim 1, wherein the isomer is a β-N—N-dimethyl[70]fulleropyrrolidinium iodide and γ-N—N-dimethyl[70]fulleropyrrolidinium iodide.

13. A N—N-dimethyl[70]fulleropyrrolidinium iodide prepared by
    (a) refluxing a $C_{70}$ fullerene, N-methylglycine, and paraformaldehyde in toluene;
    (b) evaporating the solvent after refluxing and isolating the resulting product to obtain a N-Methyl[70]fulleropyrrolidine;
    (c) dissolving the N-Methyl[70]fulleropyrrolidine in methyl iodide which results in the formation of a precipitate;
    (d) separating the precipitate from the reaction mixture; and
    (f) washing the precipitate with an organic solvent to obtain N—N-dimethyl[70]fulleropyrrolidinium iodide.

* * * * *

UNITED STATES PATENT AND TRADEMARK OFFICE
CERTIFICATE OF CORRECTION

PATENT NO. : 10,358,419 B2
APPLICATION NO. : 15/555842
DATED : July 23, 2019
INVENTOR(S) : Luis A. Echegoyen et al.

Page 1 of 1

It is certified that error appears in the above-identified patent and that said Letters Patent is hereby corrected as shown below:

In the Specification

Please add the following at Column 1, before Line 12:
STATEMENT REGARDING FEDERALLY FUNDED RESEARCH
This invention was made with government support under CHE1408865 awarded by the National Science Foundation. The government has certain rights in the invention.

Signed and Sealed this
Thirty-first Day of December, 2024

Derrick Brent
*Acting Director of the United States Patent and Trademark Office*